(12) United States Patent
Desai et al.

(10) Patent No.: US 12,358,941 B2
(45) Date of Patent: Jul. 15, 2025

(54) LIPIDIC ANALOGS OF ANTI-CANCER STEM CELL AGENT

(71) Applicant: VIRGINIA COMMONWEALTH UNIVERSITY, Richmond, VA (US)

(72) Inventors: Umesh R. Desai, Richmond, VA (US); Balaji Nagarajan, Richmond, VA (US); Connor O'Hara, Richmond, VA (US); Daniel Kwame Afosah, Richmond, VA (US); Elsamani I. Abdelfadiel, Richmond, VA (US); Jyothi Sistla, Richmond, VA (US); Rahaman Navaz Gangji, Richmond, VA (US); Ravikumar Ongolu, Richmond, VA (US); Shravan Morla, Richmond, VA (US); Viji Sankaranarayanan, Richmond, VA (US); Bhaumik B. Patel, Richmond, VA (US); Chetna Sharon, Richmond, VA (US); Rio Boothello, Richmond, VA (US); Alberto Vera, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 957 days.

(21) Appl. No.: 17/436,448

(22) PCT Filed: Mar. 6, 2020

(86) PCT No.: PCT/US2020/021308
§ 371 (c)(1),
(2) Date: Sep. 3, 2021

(87) PCT Pub. No.: WO2020/181158
PCT Pub. Date: Sep. 10, 2020

(65) Prior Publication Data
US 2022/0169673 A1    Jun. 2, 2022

Related U.S. Application Data

(60) Provisional application No. 62/966,213, filed on Jan. 27, 2020, provisional application No. 62/815,085, filed on Mar. 7, 2019.

(51) Int. Cl.
*C07J 17/00* (2006.01)
*A61K 47/54* (2017.01)
(Continued)

(52) U.S. Cl.
CPC .............. *C07J 17/00* (2013.01); *A61P 35/00* (2018.01)

(58) Field of Classification Search
CPC .......... C07J 17/00; C07J 31/006; A61P 35/00; A61K 47/55; A61K 47/554
See application file for complete search history.

(56) References Cited

FOREIGN PATENT DOCUMENTS

| | | |
|---|---|---|
| WO | 2015069979 A2 | 5/2015 |
| WO | 2017201528 A1 | 11/2017 |

OTHER PUBLICATIONS

Chu X, Tian W, Ning J, Xiao G, Zhou Y, Wang Z, Zhai Z, Tanzhu G, Yang J, Zhou R. Cancer stem cells: advances in knowledge and implications for cancer therapy. Signal Transduct Target Ther. Jul. 5, 2024;9(1):170. doi: 10.1038/s41392-024-01851-y. PMID: 38965243; PMCID: PMC11224386. (Year: 2024).*

(Continued)

*Primary Examiner* — Bruck Kifle
*Assistant Examiner* — Kevin S Martin
(74) *Attorney, Agent, or Firm* — WCF IP

(57) ABSTRACT

A group of specific sulfated flavonoid agents carrying cholesterol modification display promising in vivo anti-cancer activity through selective inhibition of cancer stem cells, and not of adult or hematopoietic stem cells. The compounds exhibit high potency, excellent oral bioavailability and a physiologically relevant therapeutic window.

11 Claims, 9 Drawing Sheets

(51) Int. Cl.
*A61K 47/55* (2017.01)
*A61P 35/00* (2006.01)
*C07J 31/00* (2006.01)

(56) References Cited

OTHER PUBLICATIONS

Dictionary.com, In Vitro, 2024, https://www.dictionary.com/browse/in-vitro (Year: 2024).*
Cecil Textbook of Medicine, 20th Ed, vol. 1, 1997 (Year: 1997).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*
Boothello, R. et al., "A Unique Nonsaccharide Method of Heparin Hexasaccharide Inhibits Colon Cancer Stem Cells via p38 MAP Kinase Activation", Molecular Cancer Therapeutics, 2018.
Patel, N. et al., "Synthetic, Non-saccharide, Glycosaminoglycan Mimetics Selectively Target Colon Cancer Stem Cells", ACS Chemical Biology 9, 2014.
Wei, X. et al., "Hyaluronic Acid-Based Nanogel-Drug Conjugates with Enhanced Anticancer Activity Designed for the Targeting of CD44-positive and Drug-Resistant Tumors", Bioconjugate Chemistry 24, 2013.

* cited by examiner

LIPIDIC ANALOGS OF ANTI-CANCER STEM CELL AGENT

This invention was made with government support under grant number P01 HL107152 awarded by the National Institutes of Health (NIH). The government has certain rights in the invention.

FIELD OF THE INVENTION

The invention is generally related to anti-cancer stem cell small molecules, their method of synthesis, and the use of these molecules for the treatment of cancer.

BACKGROUND OF THE INVENTION

The cancer stem cells (CSCs) paradigm presents a major opportunity for developing agents that offer the potential of complete cure. Tumor relapse, attributable to cancer stem cells (CSCs) that survive the first treatment of chemotherapy and/or radiation, is fairly common in colon, breast, lung, liver, renal, pancreatic, glioma and other cancers. In fact, cancer chemotherapies tend to enrich CSCs despite causing temporary tumor shrinkage which is associated with poor clinical outcomes [Martins-Neves et al., Pharmacol Res, 2018:193-204; Hu X et al., Cell Cycle, 2012:2691-2698; Lee H E et al., Br. J. Cancer, 2011: 1730-1738]. Thus, an evolving concept is to target CSCs, which is likely to not only improve outcomes following existing therapies but also achieve long-term remission and/or cure. Thus, the CSCs paradigm presents a major opportunity for developing agents that offer the potential of a complete cure.

Previous work has shown that colorectal CSCs can be selectively inhibited by a chain length-specific sequence of a glycosaminoglycan (GAG) oligomer heparin hexasaccharide (HS06) [Patel, N.J., et al., Oncotarget 2016, 7, 84608-84622]. HS06 is a non-anticoagulant sequence (see structure in FIG. 1) and no shorter or longer sequences could selectively inhibit CSC self-renewal or induce apoptosis in colorectal CSCs. Further, HS06 also inhibited pancreatic and breast CSCs, suggesting the possibility of wide-ranging therapeutic use. The structural selectivity of colorectal CSC inhibition was interestingly connected with functional selectivity, which arose from activation of p38α/β mitogen activated protein kinase (MAPK) but not other MAPKs, e.g., ERK and JNK. Further, HS06 inhibited TCF4, which is a critical regulator of CSC self-renewal, in a p38 activation dependent manner. This presented a novel paradigm for developing HS06 as an anti-CSC agent that could prevent cancer relapse.

Unfortunately, the promise of HS06 as an anticancer agent, is difficult to realize because it is prohibitively costly to prepare this agent in homogeneous form. However, significant inroads in overcoming these obstacles have been made by designing non-saccharide GAG mimetics (NSGMs), which are inexpensive and easy to synthesize mimetics. NSGMs bind strongly to GAG-binding proteins, such as growth factors, chemokines, morphogens, coagulation factors and viral glycoproteins, which enables higher selectivity and/or specificity of action [Morla, S. et al., J. Med. Chem. 2019, 62, 5501-5511; Navaz-Gangji, R. et al. ACS Med. Chem. Lett. 2018, 9, 797-802; Afosah, D., et al. J. Med. Chem. 2017, 60, 641-657; Mehta, A. Y, J. Thromb. Haemost. 2016, 14, 828-838; Patel, N. J., et al. ACS Chem. Biol. 2014, 9, 1826-33; Desai, U. R., Future Med. Chem. 2013, 5, 1363-1366].

Using a state-of-the-art orthogonal tandem screening strategy [Patel, N. et al., Methods Mol. Biol. 2015, 229, 529-41], it was discovered earlier that G2.2 (see structure in FIG. 1), a fully synthetic sulfated quercetin dimer, is a potent and selective inhibitor of colon CSCs in vitro [Patel, N.J., et al., ACS Chem. Biol., 2014, 9, 1826-1833; Desai, U R. et al., U.S. Pat. No. 9,850,221 B2]. G2.2 was identified from a library of 53 unique NSGMs as an inhibitor of colorectal CSCs, while structurally related agents called G1.4 and G4.1 (see FIG. 1) were found to be inactive in targeting CSCs. This implied high structural specificity. G2.2's effects on CSCs were mediated in part through activation of apoptotic pathways and down regulation of self-renewal factors.

G2.2 is a structural mimetic of HS06 as shown through a detailed comparison of its free solution and protein bound forms with the parent GAG [Nagarajan, B., et al., PLoS One, 2017, 12, e0171619]. Studies have shown that whereas sulfated quercetin dimers, e.g., G2.2, mimic HS06, sulfated quercetin monomers (e.g., G1.4) and trimers (e.g., G4.1) do not mimic HS06 in its recognition of growth. Such structural selectivity is indicative of a very fine-tuned modulation of one or more CSC pathways and presents a unique opportunity of developing novel therapeutics. Although G2.2 exhibits anti-CSC activity in vitro and in vivo without any major toxicity, it exhibits a modest half-life (4 hours), weak oral bioavailability (<1%), and modest potency ($IC_{50}$ 30 to 60 µM) in colon cancer spheroids.

Recently, we have shown that the in vitro activity translates well to in vivo function. G2.2 was able to reduce the growth of HT29 and HCT116-based colon xenografts, induced by CSCs (CD133+/CXCR4+, Dual hi), in a dose-dependent fashion [Boothello, R., et al., Mol. Cancer Ther. 2019, 18, 51-56]. More importantly, G2.2 also significantly delayed the growth of colon xenografts induced with cancer cells first treated with oxaliplatin and 5-fluorouracil. These conditions attempt to resolve disease relapse, wherein the treatment of cancer with chemotherapy results in accumulation of CSCs that reactivate later.

Measurement of CSC markers, such as CD133, DCMLK1, LGR5, and LRIG1, showed that G2.2 robustly inhibited CSCs. Likewise, self-renewal, as measured by secondary, tertiary, and quaternary spheroid growth from xenograft cells, was also attenuated. G2.2 induced apoptosis only in Dual hi CSCs in vivo alluding to its CSC targeting effects. A key result of translational value was that G2.2 displayed no adverse consequences, as indicated through morphologic and biochemical studies of vital organ functions, blood coagulation profile, and ex vivo analyses of normal intestinal (and bone marrow) progenitor cell growth. Finally, in the manner of HS06, G2.2's inhibition of CSC self-renewal was mediated through activation of p38alpha MAPK and inhibition of ERK1/2. [Boothello, R., et al., Mol. Cancer Ther. 2019, 18, 51-56].

SUMMARY OF THE INVENTION

Provided herein are compounds for the treatment of cancer, and methods of making the compounds. In particular, the compounds are designed to target and kill cancer cells such as cancer stem cells (CSCs) that seed tumors and survive chemotherapy and/or radiation therapy. The compounds comprise a synthetic sulfated quercetin dimer conjugated to a cholesterol molecule. In some aspects, the synthetic sulfated quercetin dimer is G2.2.

Some embodiments relate to a compound having a formula:

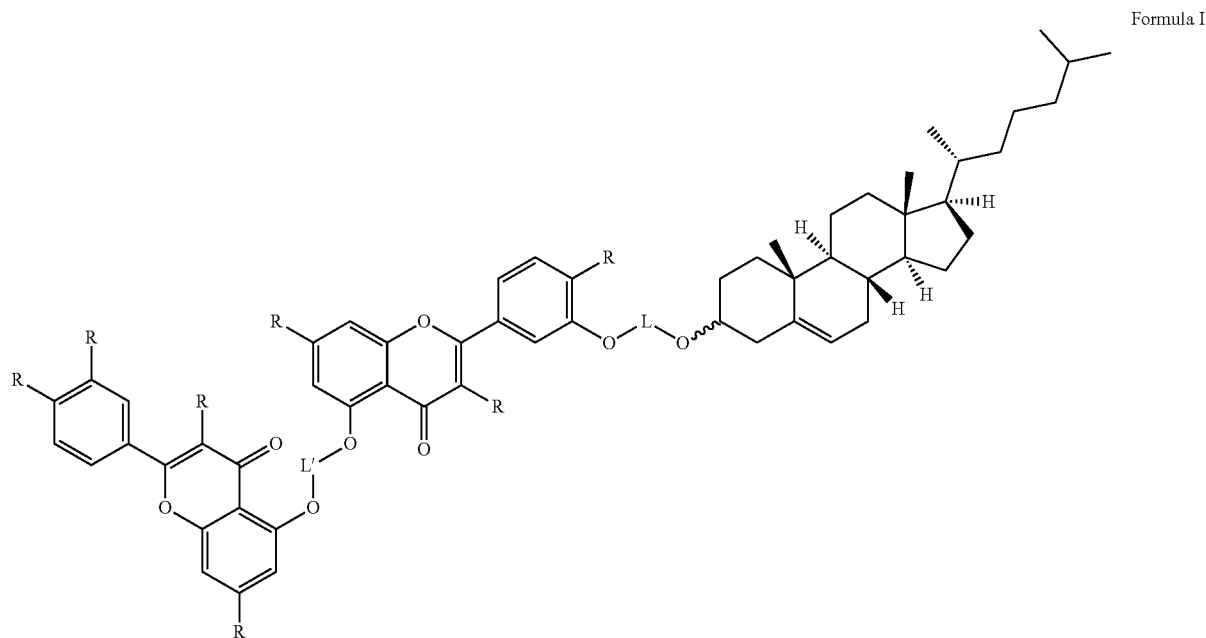

Formula I or a pharmaceutically acceptable salt, solvate or hydrate thereof, wherein, R can be the same or different at each location and is a hydrogen, —OH, or —OSO$_3^-$M$^+$ with the caveat that at least one R is —OSO$_3^-$M$^+$, wherein M$^+$ is a cation, examples of which include but are not limited to Na$^+$, K$^+$, Li$^+$, Ca$^{2+}$, and NG$_4^+$, wherein G is H, an alkyl group, alicyclic group, or an aryl group, and L and L' can be the same or different at each location and is a linker selected from of one of the following:

L1

—(CH$_2$)$_n$—

L2

—[O—CH$_2$CH$_2$—O]$_n$—

L3

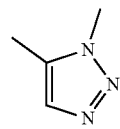

L4

—CH$_2$CH=CHCH$_2$—

L5

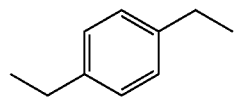

-continued

L6

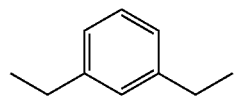

L7

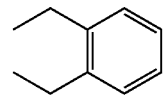

L8

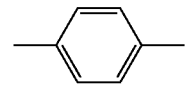

L9

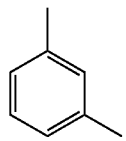

L10

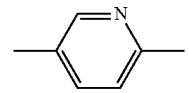

L11

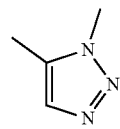

L12

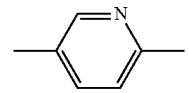

L13
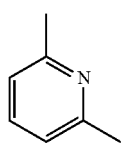
L14
L15
L16
L17
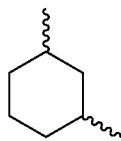
L18
L19
wherein n is an integer from 1 to 18, and where the curved/wavy line indicates the presence of a bond of undefined stereochemistry and can be the same or different at each location.
In some aspects, the compound of claim 1 has the structure of Formula II:
Formula II wherein,
n is an integer from 0 to 18;
where the curved line indicates the presence of a bond of undefined stereochemistry; and
$M^+$ is a cation, examples of which include but are not limited to $Na^+$, $K^+$, $Li^+$, $Ca^{2+}$, and $NG_4^+$, wherein G is H, an alkyl group, alicyclic group, or an aryl group In some embodiments, the compound of Formula I may be a compound having the structure of Formula II:

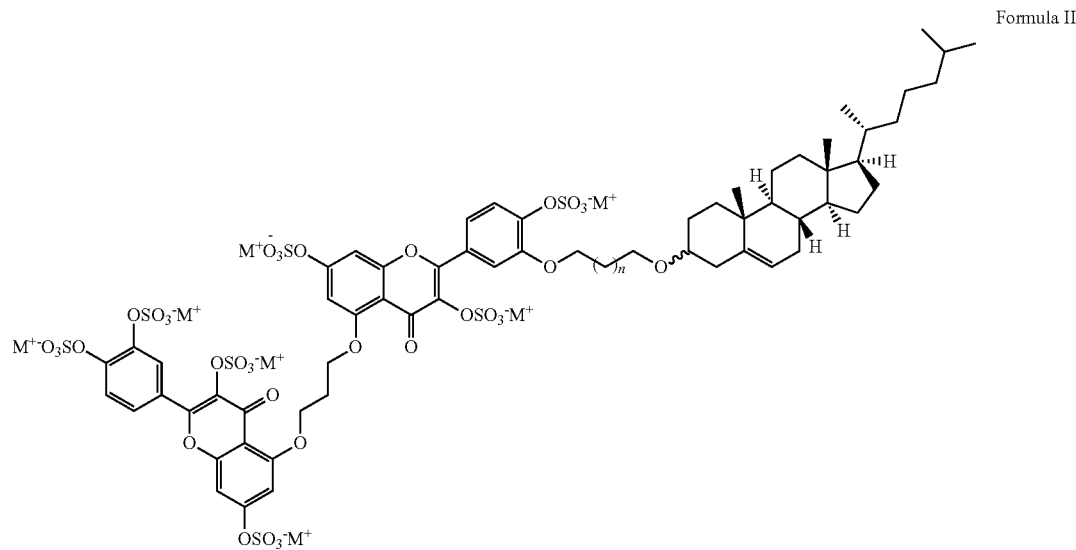

Formula II wherein,
n is an integer from 0 to 18;
where the curved line indicates the presence of a bond of undefined stereochemistry; and
$M^+$ is a cation, examples of which include but are not limited to $Na^+$, $K^+$, $Li^+$, $Ca^{2+}$, and $NG_4^+$, wherein G is H, an alkyl group, alicyclic group or an aryl group In some embodiments, the compound of Formula II has the formula:

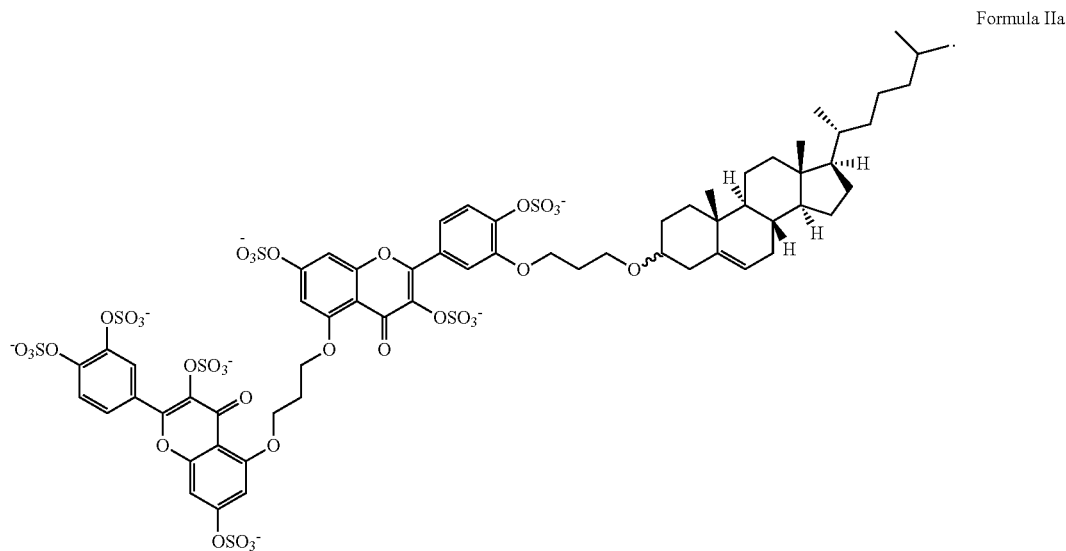

Formula IIa

In some embodiments, the compound of Formula II has the formula:
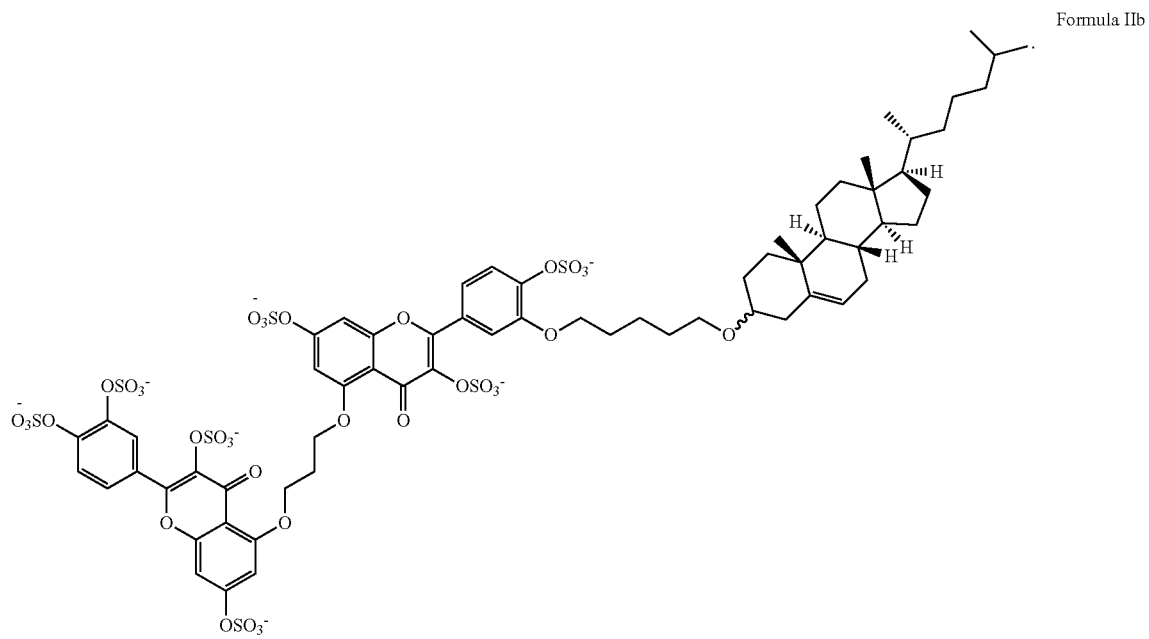
Formula IIb
In some embodiments, the compound of Formula II has the formula:
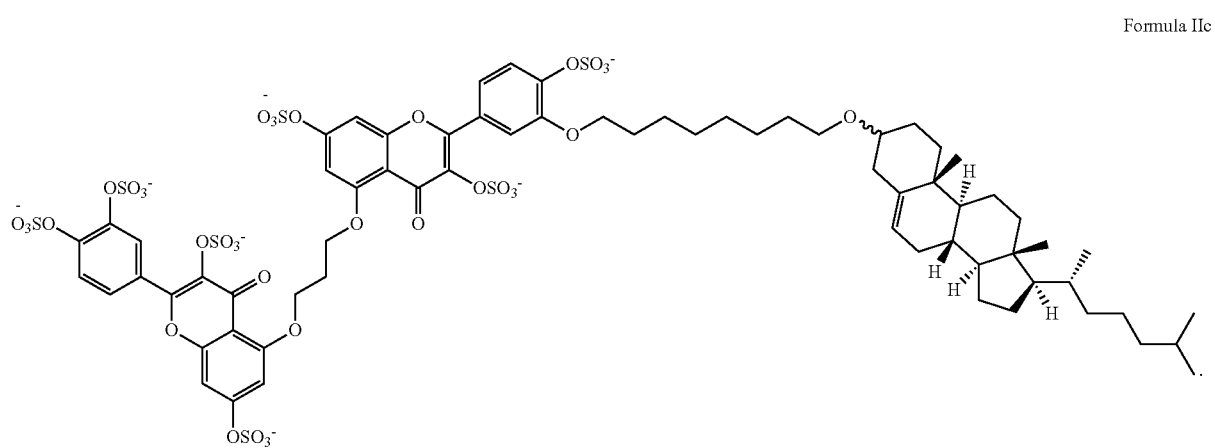
Formula IIc In some embodiments, the compound of Formula I may be a compound having the structure of Formula III:

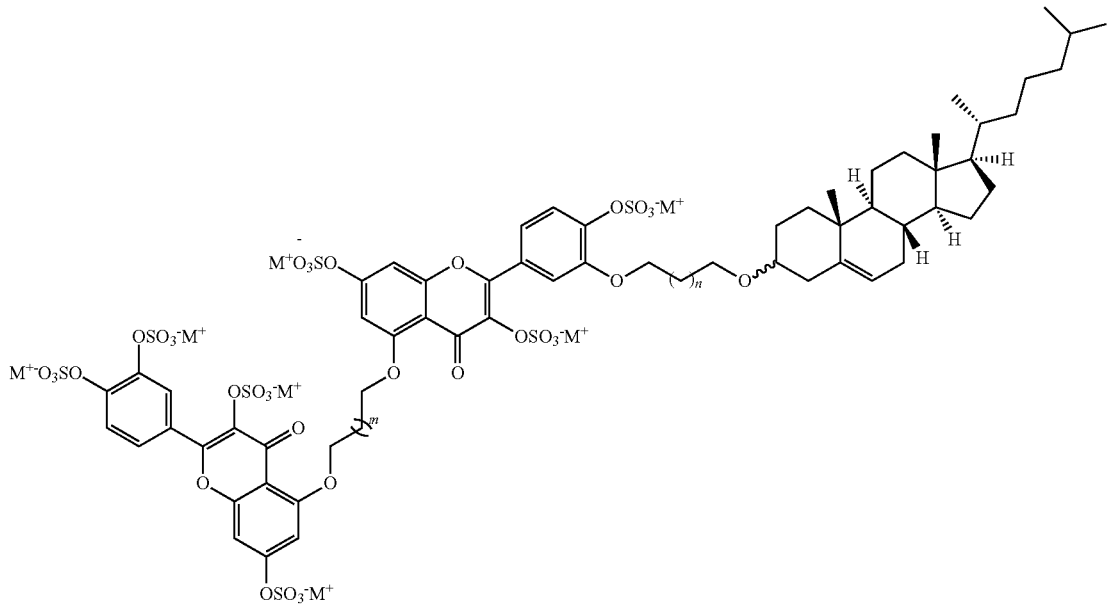

Formula III wherein,
  n is an integer from 1 to 18;
  m is an integer from 1 to 18;
  where the curved line indicates the presence of a bond of undefined stereochemistry; and
  $M^+$ is a cation, examples of which include but are not limited to $Na^+$, $K^+$, $Li^+$, $Ca^{2+}$, and $NG_4^+$, wherein G is H, an alkyl group, alicyclic group or an aryl group.

In some embodiments, a pharmaceutical composition comprising the compound of Formula I, or a salt, solvate or hydrate thereof, and a pharmaceutically acceptable carrier are provided.

In some embodiments, a method for treating cancer is provided comprising administering to a subject in need thereof an effective amount of a compound of Formula (I), or a salt, solvate or hydrate thereof.

In some embodiments, the subject is mammalian.
In some embodiments, the subject is human.
In some embodiment, the cancer is selected from the group consisting of colon cancer, breast cancer, liver cancer, lung cancer, renal cancer, pancreatic cancer and glioma.

In some embodiments, a method of killing or inhibiting the growth of a cancer stem cell is provided, comprising contacting the cancer stem cell with an effective amount of the compound of Formula (I), or a salt, solvate or hydrate thereof.

In some embodiments, the cancer stem cell is mammalian.
In some embodiments, the cancer stem cell is human.
In some embodiments, the cancer stem cell is in vitro.
In some embodiments, the cancer stem cell is in vivo.
In some embodiments, the cancer stem cell is from a cancer selected from the group consisting of colon cancer, breast cancer, lung cancer, liver cancer, renal cancer, pancreatic cancer and glioma.

DETAILED DESCRIPTION

Figure 1:
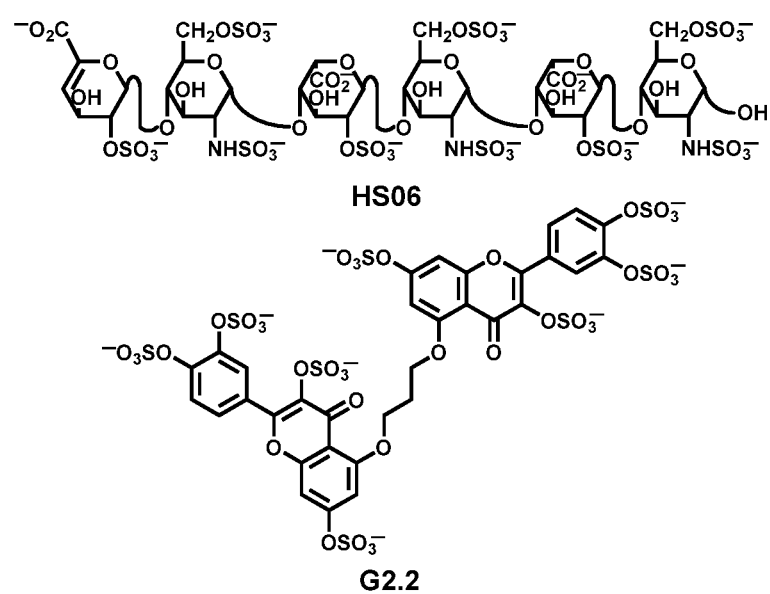
FIG. 1. Structures of HS06 and G2.2.

The following descriptions and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

As described herein, lipid-modified sulfated quercetin molecules were designed to add cholesterol to the quercetin dimer through a carbon-linker by substituting a sulfate that was found to be dispensable for the action of G2.2. The rational design of the lipid-modified analogs of G2.2 followed rigorous pharmaceutical principles to conjugate cholesterol to the parental G2.2 molecule without compromising its interaction with its protein target(s). Such lipid-modified molecules were intended to increase half-life of G2.2 in circulation, enhance its oral bioavailability, enhance its interactions with the target protein by engaging hydrophobic pockets in the molecules and/or facilitating G2.2's localization in the lipid rafts.

Definitions

As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. R groups at different locations may be the same or different.

As used herein, any "G" group(s) represent substituents that can be attached to the indicated atom. A G group may be substituted or unsubstituted. G groups at different locations may be the same or different.

As used herein, "alkyl" refers to a straight or branched hydrocarbon chain that includes a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "C1-C6 alkyl" or similar designations. By way of example only, "C1-C6 alkyl" indicates that there are one to four carbon atoms in the alkyl chain, i.e., the alkyl chain is selected from methyl, ethyl, propyl, isopropyl, n-butyl, isobutyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "alicyclic" refer to relating to an organic compound which combines cyclic structure with aliphatic properties, e.g. a saturated cyclic hydrocarbon, examples of which include but are not limited to: alicyclic groups having 3 to 12 carbon atoms such as a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, and an adamantyl group, or the like.

CSC: Cancer Stem cell.

NSGM: Non-saccharide GAG mimetic.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvates forms with pharmaceutically acceptable solvents such as water, ethanol, or the like. In other embodiments, the compounds described herein exist in unsolvated form. Solvates contain either stoichiometric or non-stoichiometric amounts of a solvents and may be formed during the process of crystallization with pharmaceutically acceptable solvent such as water, ethanol, or the like. Hydrates are formed when the solvent is water, or alcoholates are formed when the solvent is alcohol. In addition, the compound provided herein can exist in unsolvated as well as solvated forms. In general, the solvated forms are considered equivalent to the unsolvated form for the purpose of the compounds and methods provided herein.

Where a range of values is provided, it is understood that the upper and lower limit, and each intervening value between the upper and lower limit of the range is encompassed within the embodiments.

Synthetic Methods

In some embodiments, a solution of cholesterol (1 eq.) in DCM treated with 4-toluenesulfonylchloride (1.5 eq.) in the presence of 1.5 eq. of triethylamine and 0.05 eq. of 4-dimethylaminopyridine to afford a cholesterol tosylate. The cholesterol tosylate was added to a diol such as, but not limited to diethyl glycol or triethylene glycol, 1,4-butanediol, 1,5-pentanediol, 1,6-hexanediol, 1,7-heptanediol, 1,8-octanediol, 1,9-nonanediol or 1,10-decanediol form intermediate 1b. The intermediate is tosylated to form 1c. A triprotected quercetin is coupled to the tosylated lipid to form an intermediate 1d. 1d is dimerized through the addition of 1 eq. of 2-(3,4-bis(methoxymethoxy)phenyl)-5-(3-bromopropoxy)-3,7-bis(methoxymethoxy)-4H-chromen-4-one for produce 1e. The global deprotection of 1e followed by its sulfonation of the desired lipid modified analogs of Formula II.

Other protecting groups may be used in a similar manner, such as but not limited to methyl, methoxymethyl, benzoyl, benzyl, silyl (e.g., t-butyl-di-methyl-silyl, etc.), p-methoxybenzyl, etc.

Certain compounds provided herein can be prepared according to the following synthesis scheme.

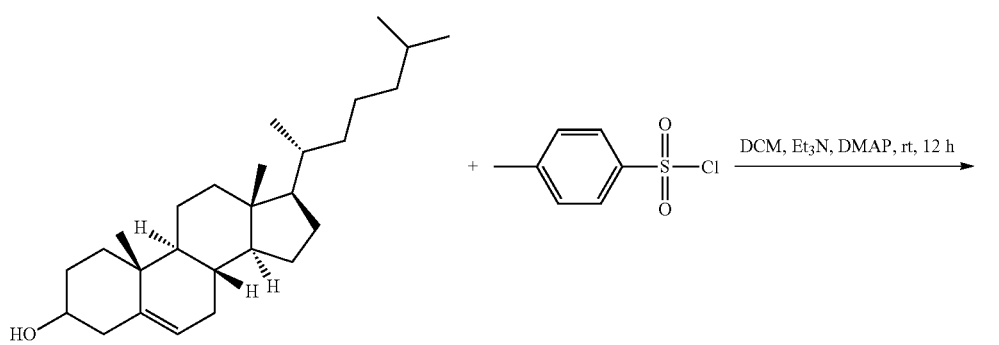

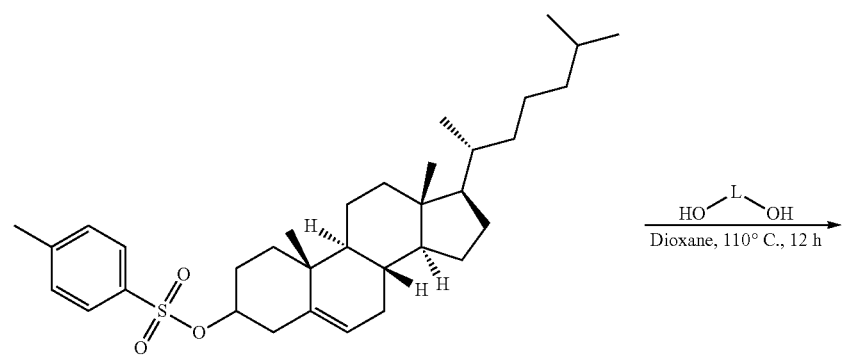

1a

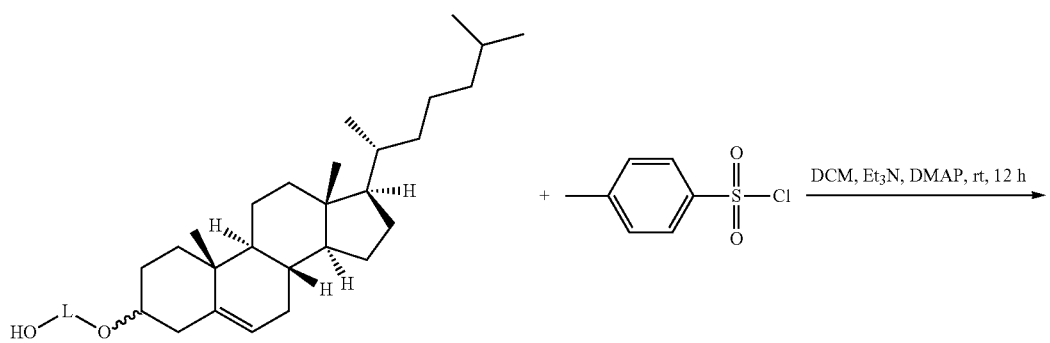

1b

-continued
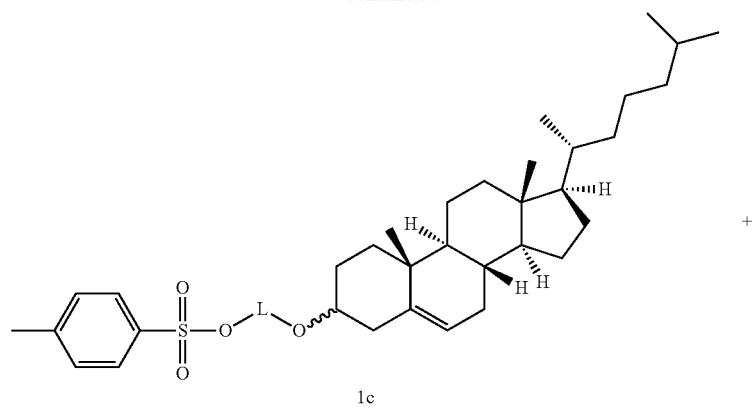
1c
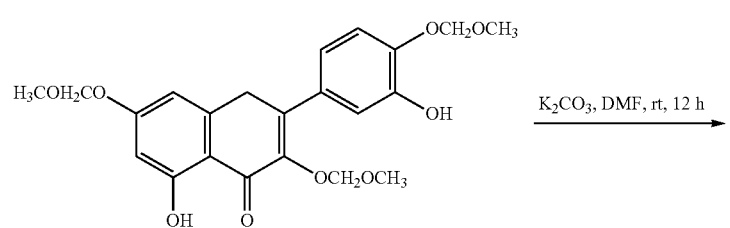
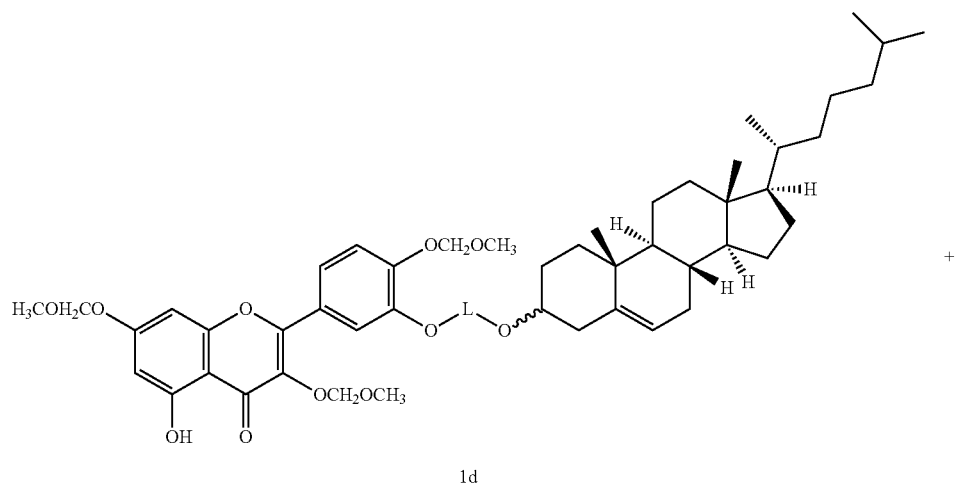
1d
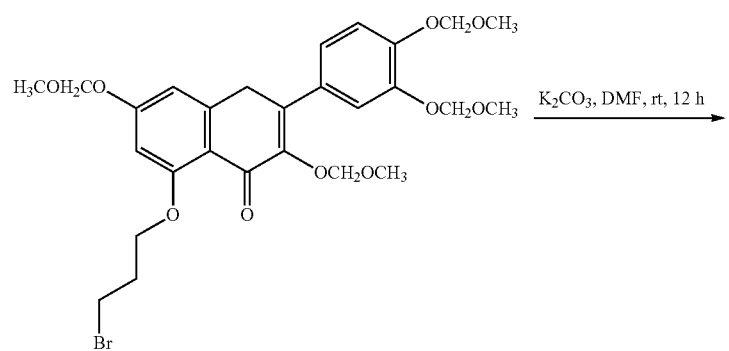

-continued
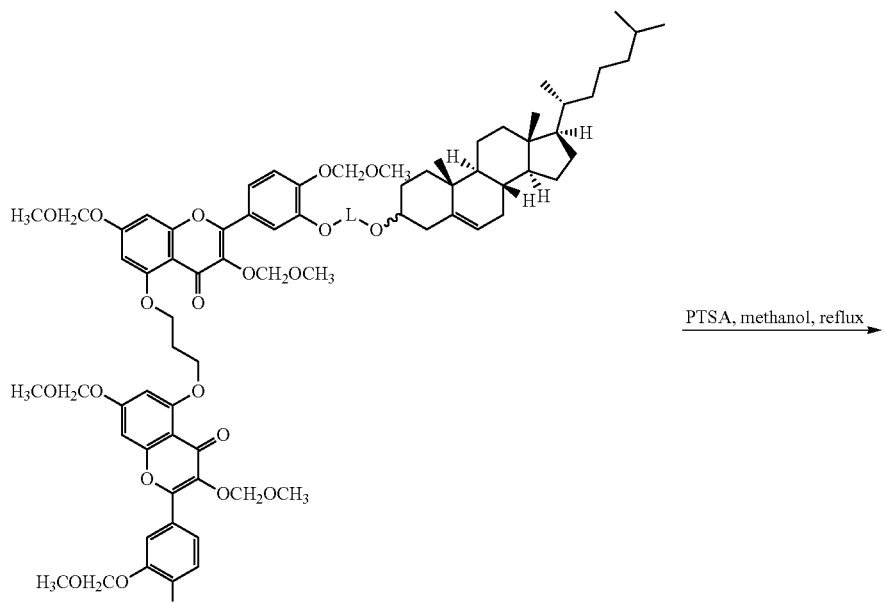
1e
PTSA, methanol, reflux →
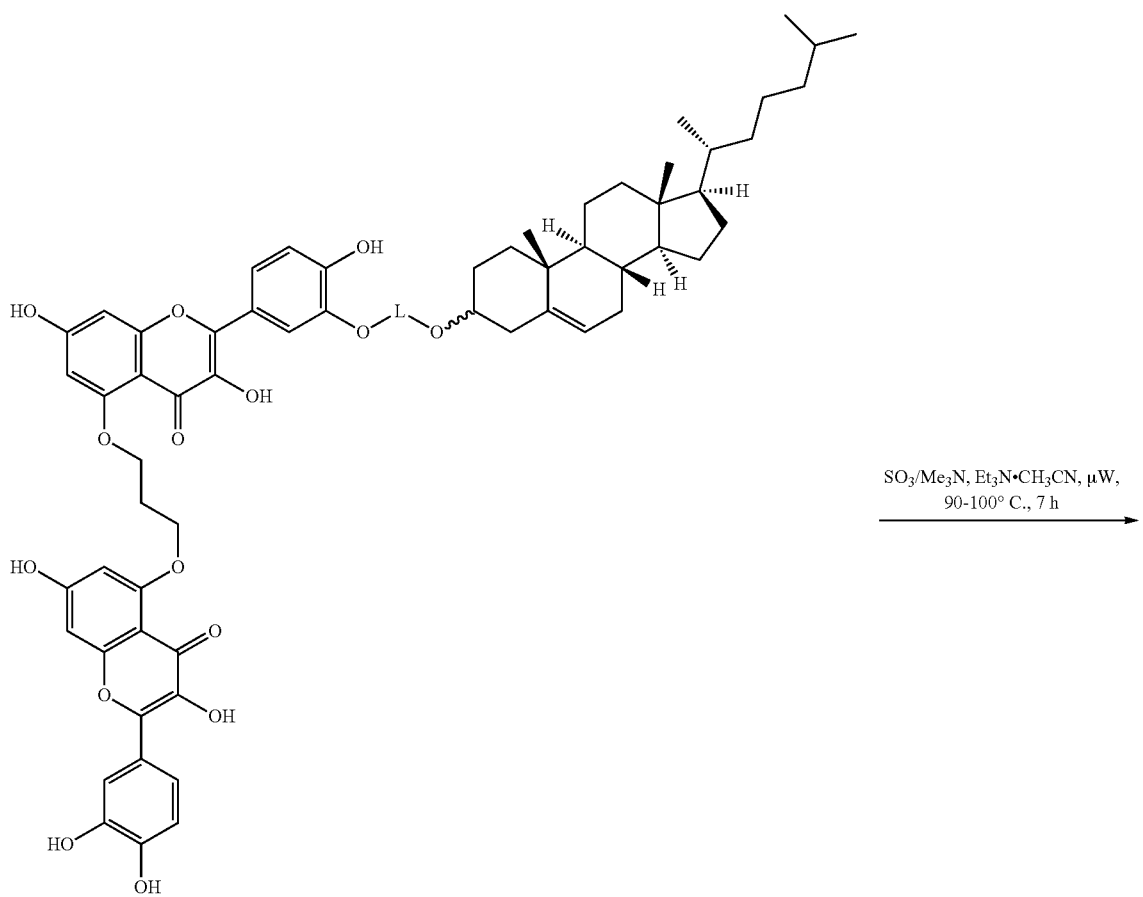
1f
SO$_3$/Me$_3$N, Et$_3$N•CH$_3$CN, μW, 90-100° C., 7 h →

-continued
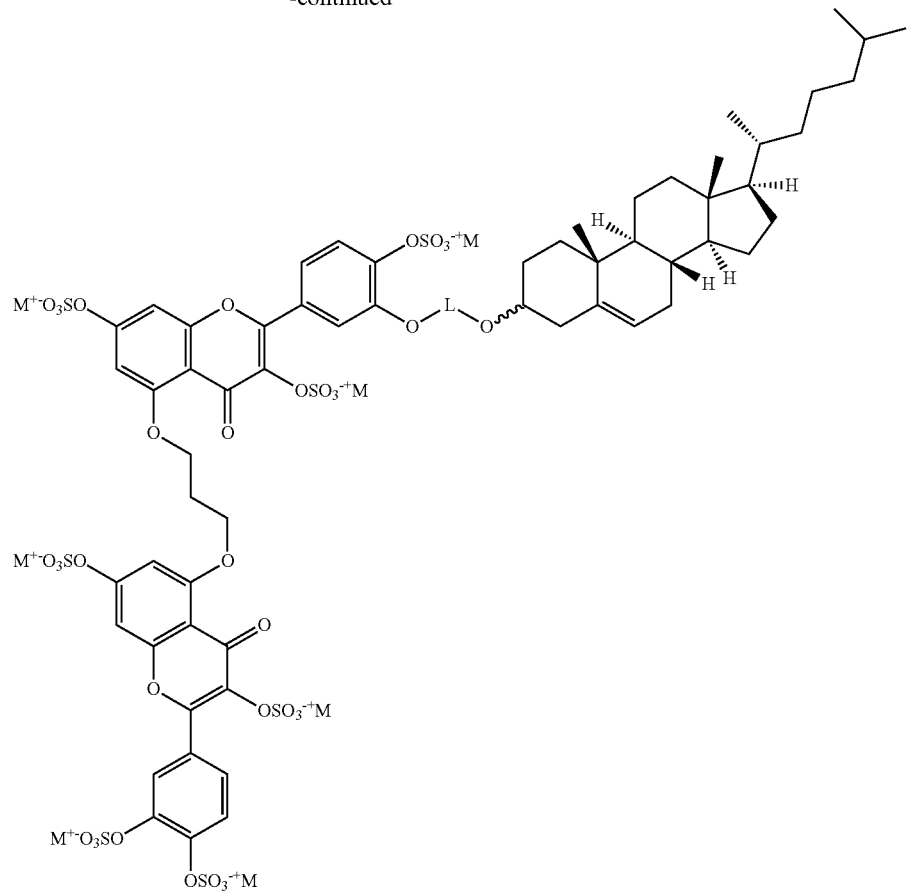
wherein,
wherein $M^+$ is a cation, examples of which include but are not limited to $Na^+$, $K^+$, $Li^+$, $Ca^{2+}$, and $NG_4^+$, wherein G is H, an alkyl group, alicyclic group or an aryl group; and
L is a linker selected from of one of the following:
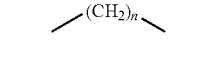 L1
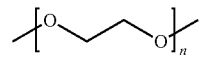 L2
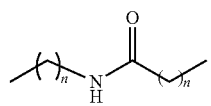 L3
 L4
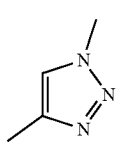 L5
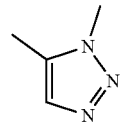 L6
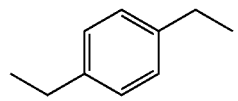 L7
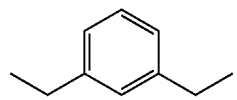 L8
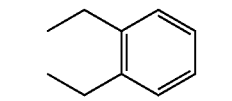 L9
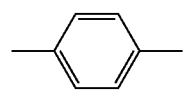 L10

23
-continued
L11
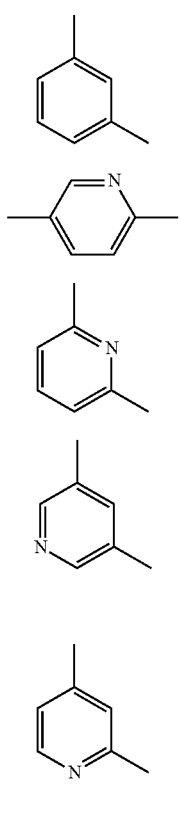
L12
L13
L14
L15
L16
24
-continued
L17
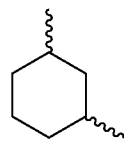
L18
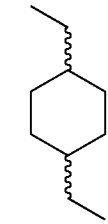
L19
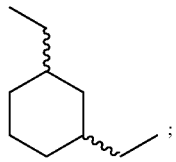
wherein n is an integer from 1 to 18, and
wherein the curved line indicates the presence of a bond of undefined stereochemistry which can be the same or different at each location (e.g., a bond (R or S) to a methyl moiety).
Exemplary Compounds
Certain compounds provided herein include compounds having a formula:
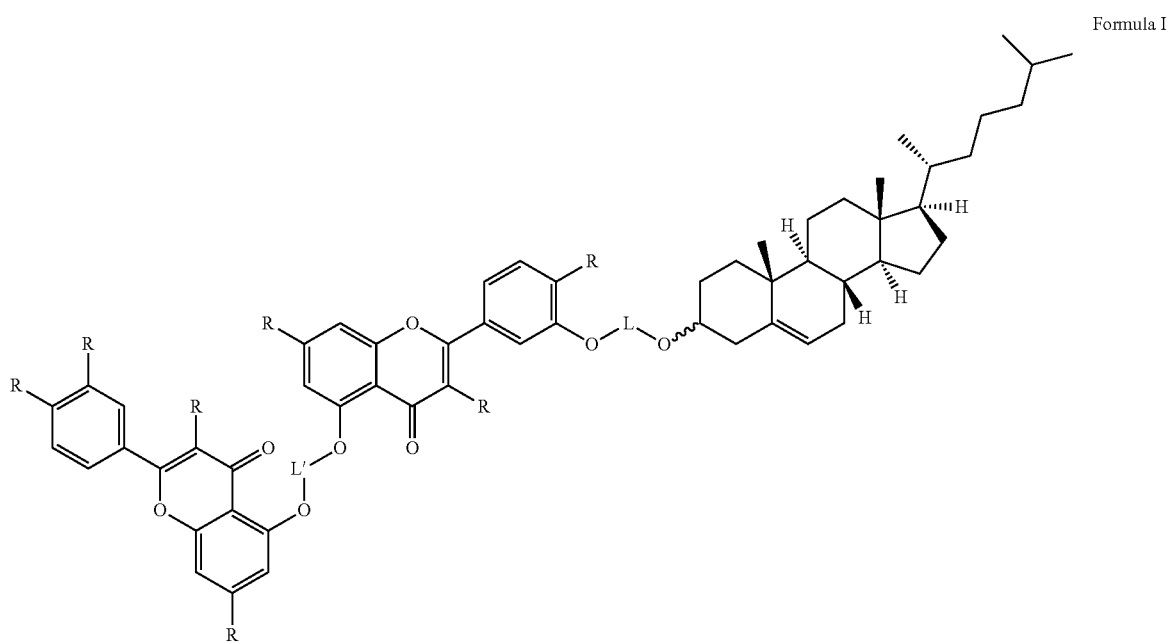
Formula I or a pharmaceutically acceptable salt, solvate, or hydrate thereof, wherein, R can be the same or different at each location and is a hydrogen, —OH, or —OSO$_3^-$M$^+$ with the caveat that at least one of the R is —OSO$_3^-$M$^+$; wherein M$^+$ is a cation, examples of which include but are not limited to Na$^+$, K$^+$, Li$^+$, Ca$^{2+}$, and NG$_4^+$, wherein G is H, an alkyl group, alicyclic group or an aryl group; and L and L' can be the same or different at each location and is a linker selected from one of the following:

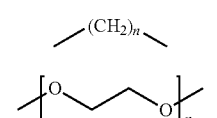
L1

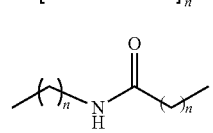
L2

L3

L4

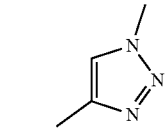
L5

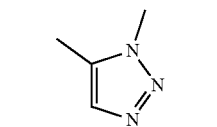
L6

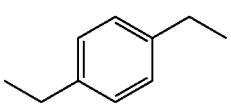
L7

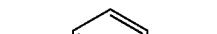
L8

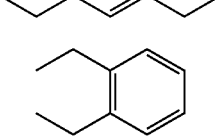
L9

L10

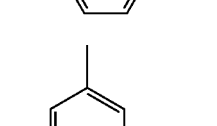
L11

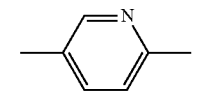
L12

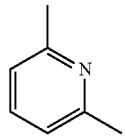
L13

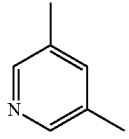
L14

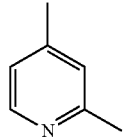
L15

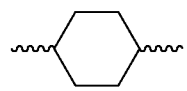
L16

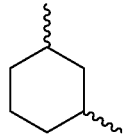
L17

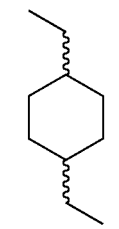
L18

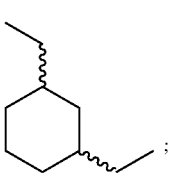
L19 wherein n is an integer from 1 to 18, and wherein the curved line indicates the presence of a bond of undefined stereochemistry (e.g. R or S) which can be the same or different at each location.

In some aspects, the compound of Formula I has the structure of Formula II:

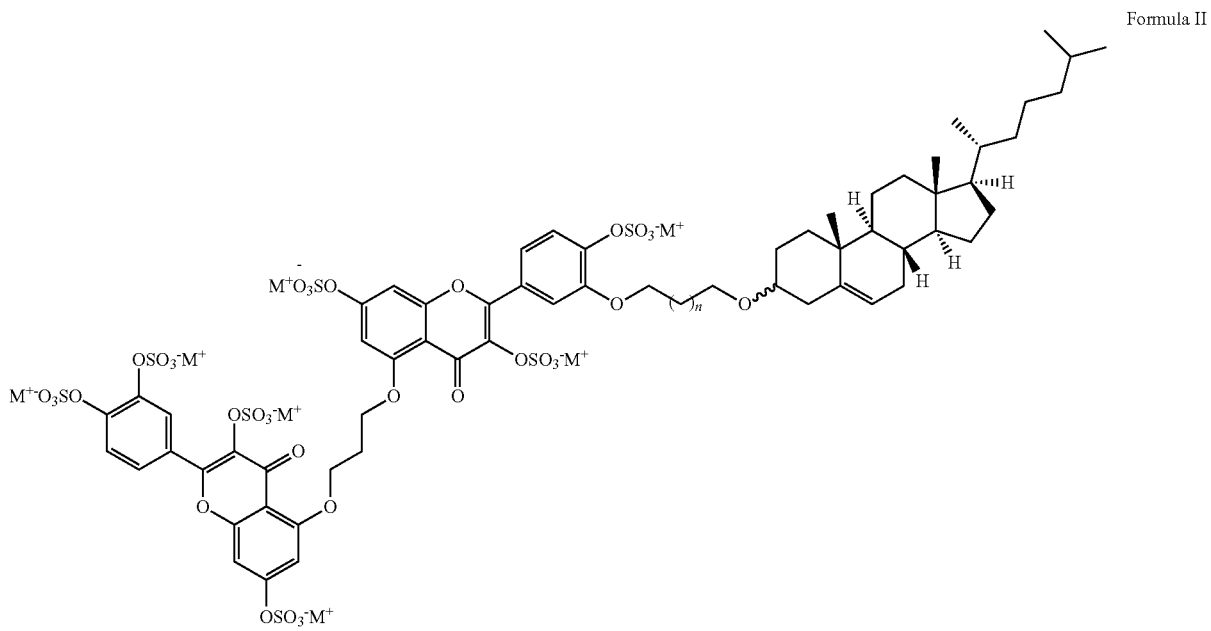

Formula II wherein,
n is an integer from 0 to 18,
wherein the curved line indicates the presence of a bond of undefined stereochemistry; and
$M^+$ is a cation, examples of which include but are not limited to $Na^+$, $K^+$, $Li^+$, $Ca^{2+}$, and $NG_4^+$, wherein G is H, an alkyl group, alicyclic group, or an aryl group.

In some embodiments, the compound of Formula II has the formula:

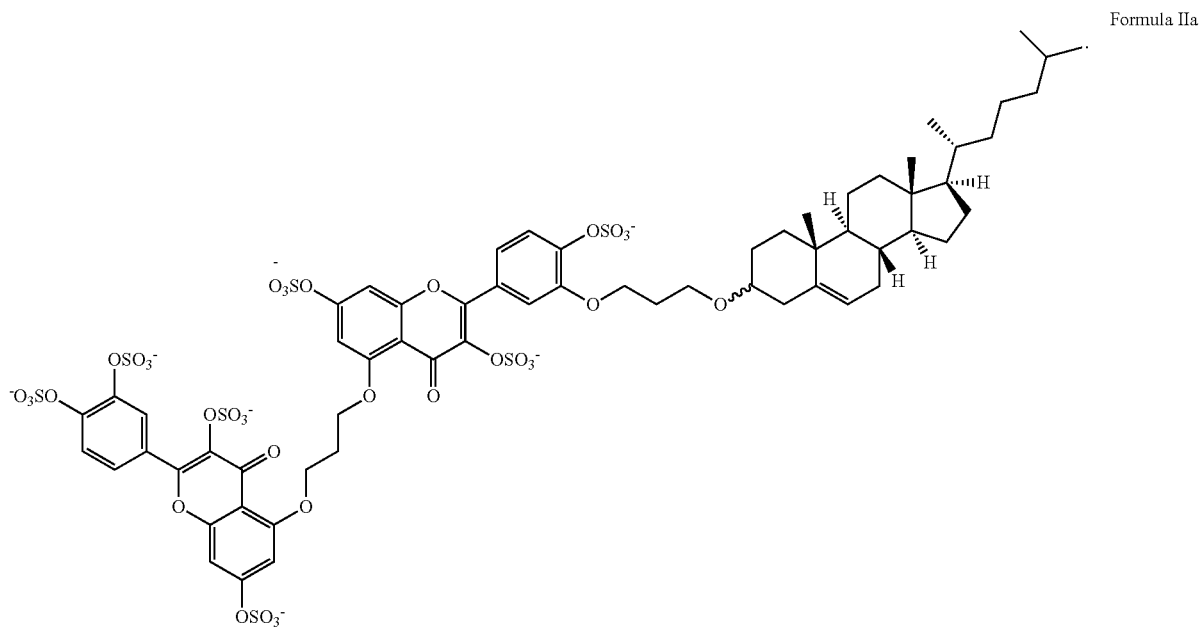

Formula IIa

In some embodiments, the compound of Formula II has the formula:
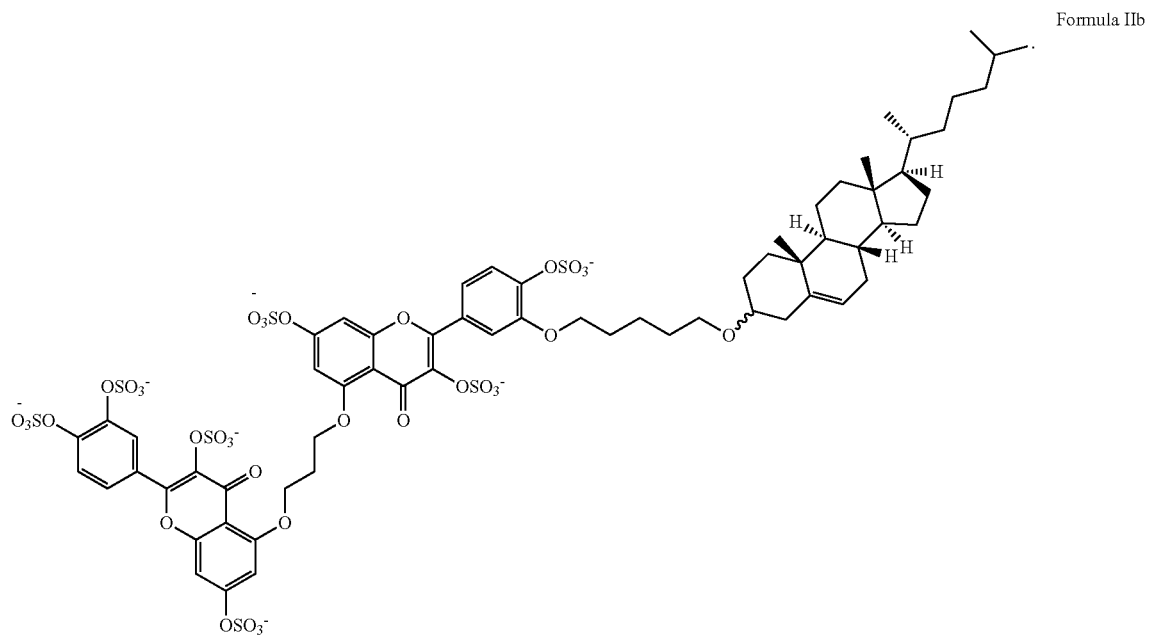
Formula IIb
In some embodiments, the compound of Formula II has the formula:
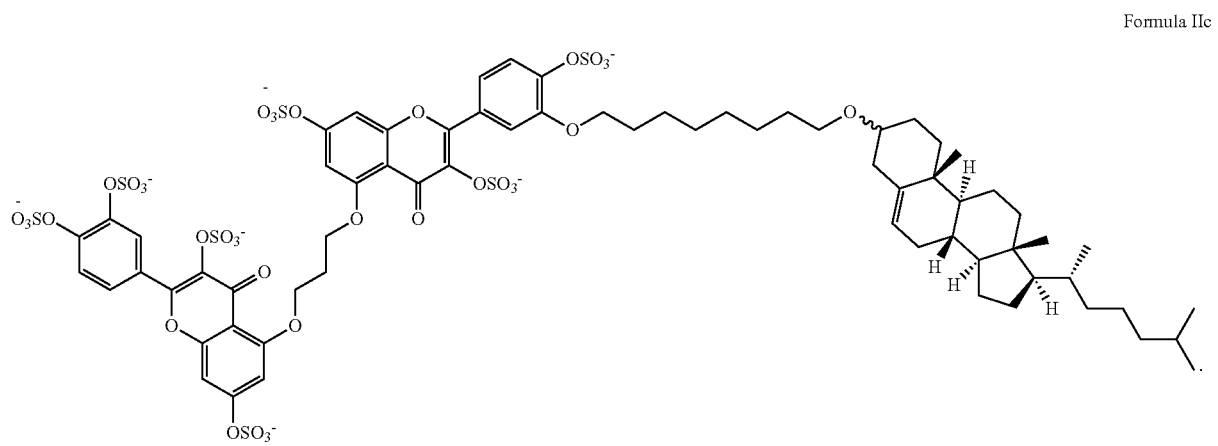
Formula IIc In some embodiments, the compound of formula I is a compound having the structure of Formula III:

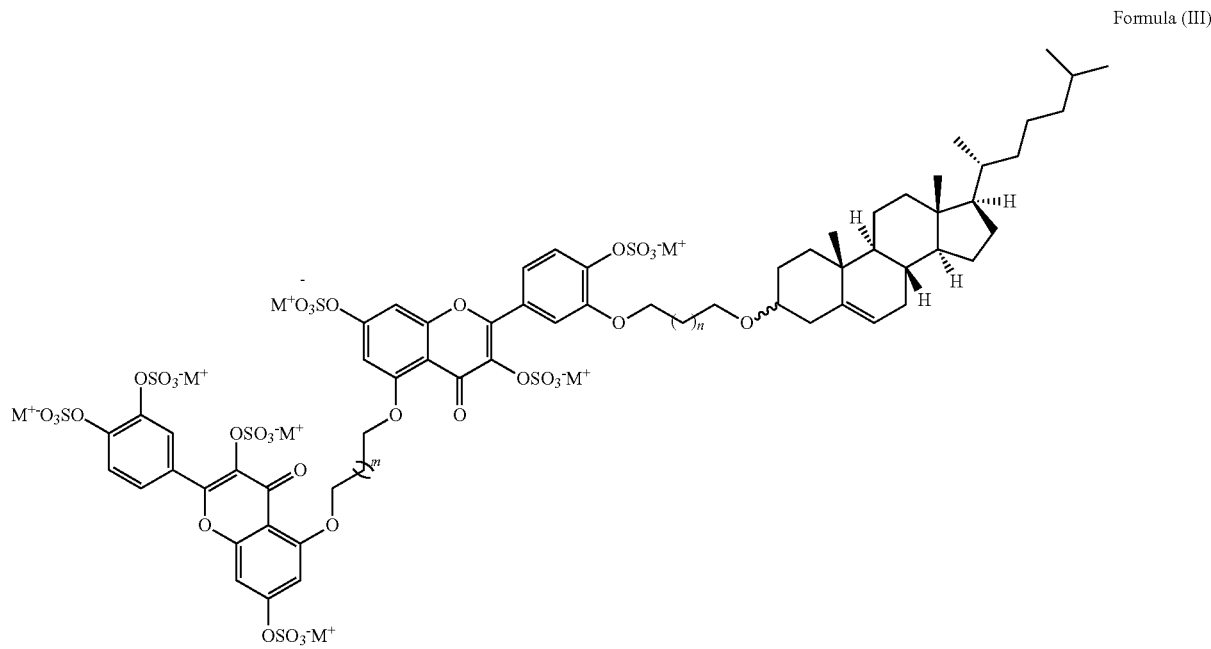

Formula (III)

wherein,
n is an integer from 1 to 18;
wherein the curved line indicates the presence of a bond of undefined stereochemistry;
m is an integer from 1 to 18; and
$M^+$ is a cation, examples of which include but are not limited to $Na^+$, $K^+$, $Li^+$, $Ca^{2+}$, and $NG_4^+$, wherein G is H, an alkyl group, alicyclic group or an aryl group.

The compounds can be in the form of a pharmaceutically acceptable salt. The term "pharmaceutically acceptable salt" as used herein is a broad term, and is to be given its ordinary and customary meaning to a person of ordinary skill in the art (and is not to be limited to a special or customized meaning), and refers without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity.

The compounds can be in amorphous form, or in crystalline forms. The crystalline forms of the compounds can exist as polymorphs, which are included in preferred embodiments. In addition, some of the compounds may also form solvates or hydrates with water or other organic solvents. Such solvates are similarly included within the scope of the disclosure.

Pharmaceutical Compositions

It is generally preferred to administer the compounds in an intravenous or subcutaneous unit dosage form; however, other routes of administration are also contemplated. Contemplated routes of administration include but are not limited to oral, parenteral and intratumoral. The compounds can be formulated into liquid preparations for, e.g., oral administration. Suitable forms include suspensions, syrups, elixirs, and the like. Particularly preferred unit dosage forms for oral administration include tablets and capsules. Unit dosage forms configured for administration once a day are particularly preferred; however, in certain embodiments it can be desirable to configure the unit dosage form for administration twice, or more, a day; every other day; or three times a week; or once a week.

The pharmaceutical compositions are preferably isotonic with the blood or other body fluid of the recipient. The isotonicity of the compositions can be attained using sodium tartrate, propylene glycol or other inorganic or organic solutes. Sodium chloride may be preferred in some embodiments. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The compounds can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, coloring agents, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the compounds can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 99 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, 45, 50, 55, 60, 65, 70, 75, 80, 85, 90, 95 or more wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered inhibitor moistened with an inert liquid diluent.

Preferably, each tablet or capsule contains from about 0.1 mg or less to about 1,000 mg or more of at least one compound, more preferably from about 10, 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms. Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of inhibitor doses When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or *arachis* oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery can also be employed. The compound is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of compound. Typically, each formulation is specific to the type of device employed and can involve the use of an appropriate propellant material, in addition to diluents, adjuvants, and/or carriers useful in therapy.

The compound and/or other optional active ingredients are advantageously prepared for pulmonary delivery in particulate form with an average particle size of from $0.1\mu m$ or less to $10\mu m$ or more, more preferably from about 0.2, 0.3, 0.4, 0.5, 0.6, 0.7, 0.8, or $0.9\mu m$ to about 1.0, 1.5, 2.0, 2.5, 3.0, 3.5, 4.0, 4.5, 5.0, 5.5, 6.0, 6.5, 7.0, 7.5, 8.0, 8.5, 9.0, or $9.5\mu m$. Pharmaceutically acceptable carriers for pulmonary delivery of inhibitor include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the inhibitor dissolved or suspended in water at a concentration of about 0.01 or less to 100 mg or more of inhibitor per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the inhibitor caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Preferred propellants include trichlorofluoromethane, dichlorodifluoromethane, dichlorotetrafluoroethanol, 1,1,1, 2-tetrafluoroethane, and combinations thereof. Suitable surfactants include sorbitan trioleate, soya lecithin, and oleic acid.

Formulations for dispensing from a powder inhaler device typically comprise a finely divided dry powder containing inhibitor, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When a compound of the preferred embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The compounds can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, chemotherapeutics and the like), or can contain materials useful in physically formulating various dosage forms of the preferred embodiments, such as excipients, dyes, thickening agents, stabilizers, preservatives or antioxidants. Anti-cancer agents that can be used in combination with the compounds of preferred embodiments include, but are not limited to, vinca alkaloids such as vinblastine and vincristine; anthracyclines such as doxorubicin, daunorubicin, epirubicin; anthracenes such as bisantrene and mitoxantrone; epipodophyllo-toxins such as etoposide and teniposide; and other anticancer drugs such as actinomyocin D, mithomycin C, mitramycin, methotrexate, docetaxel, etoposide (VP-16), paclitaxel, docetaxel, and adriamycin); and immunosuppressants (e.g., cyclosporine A, tacrolimus).

Therapeutic Methods

Some embodiments provided herein relate to methods of treating cancer such as but not limited colon cancer, lung cancer, liver cancer, breast cancer, renal cancer, pancreatic cancer, and glioma, e.g. by eradicating cancer stem cells. In general, the methods involve administering an effective amount of a compound of formula I or a pharmaceutically acceptable salt, solvate or hydrate thereof, to a subject in need thereof. The subject may be a mammal, such as a human, but veterinary usage is also encompassed. The cancer that is treated can be any type of cancer, examples of which include but are not limited to: colon cancer, breast cancer, liver cancer, lung cancer, renal cancer, pancreatic cancer and glioma.

Also provided are methods of killing or inhibiting the growth of cancer stem cells. The methods generally comprising a step of contacting a cancer stem cell with an amount of the compound of Formula (I) that is sufficient to kill or inhibit the growth of the cell. The cancer stem cell may be mammalian, e.g. human, and may be in vitro or in vivo, and may be from any type of cancer, examples of which include but are in no way limited to colon cancer, breast cancer, lung cancer, liver cancer, renal cancer, and glioma.

EXAMPLES

Example 1. Design of Cholesterol-Derivatives of G2.2

Drugs conjugated with steroids such as cholesterol have shown advantages of reduced adverse consequences. One reason why side effects decrease is because of improved tumor targeting, which arises from overexpression of low-density lipoprotein receptors (LDLR) on cancer cells [Gueddar, N., et al., *Biochimie* 1993, 75, 811-819; Maletinska, L., et al., Cancer Res. 2000, 60, 2300-2303]. This reduces the amount necessary to invoke the same level of anti-cancer activity. Although advantageous, cholesterol-derivatization could become a liability too. For example, cholesterol can enhance cell and nucleus penetration [Ding, Y, et al. *Bio-materials* 2012, 33, 8893-8905], which could alter cellular signaling with deleterious consequences. Cholesterol is also extensively oxidized by cytochrome P450s [e.g., CYP7A1, CYP27A1, CYP46A1, etc.], which could enhance liability in terms of metabolites. Finally, cholesterol has a unique hydrophobic structure, which may alter the protein targeting and binding properties of the agent being conjugated. Despite these liabilities, cholesterol-derivatization of a potential anti-cancer agent is a potentially rewarding concept. Thus, we reasoned that it is necessary to design an optimal cholesterol-derivative of G2.2, which could enhance targeting of lipid rafts on cell membranes, improve pharmacokinetic properties and enhance anti-CSC potency, thereby further contributing to anti-cancer activity.

Modification of G2.2 with one cholesterol unit requires identification of where to covalently conjugate it on G2.2 structure. There are at least 10 possible positions on the G2.2 scaffold that could be derivatized with cholesteryl moiety. Further, the length and nature of the linker between G2.2 and cholesteryl moiety are also likely to be important. In fact, the literature utilizes various types of linkers for preparing conjugates of drugs including alkyl-based, glycol-based, amide-based, or ester-based. Thus, to arrive at a well-reasoned structure of G2.2-cholesterol conjugate, we performed comprehensive computational studies of several different analogs to yield insight into the most optimal analogs to pursue.

Molecular dynamics (MD) simulations identified the suitable modification sites for G2.2. To assess the fitness of the docked structures, G2.2 complexes with FGF2, FGFR1, and FGFR1-FGF2 obtained from GOLD were prepared for molecular dynamics. AMBER-ff99SB force field was utilized for the protein receptors, the overall charge was neutralized and then the complexes placed in the center of a TIP3P cuboid water box with minimum distance of 12 Å between the box wall to any atom of the complex. MD simulations were performed using AMBER14.

Figure 2:
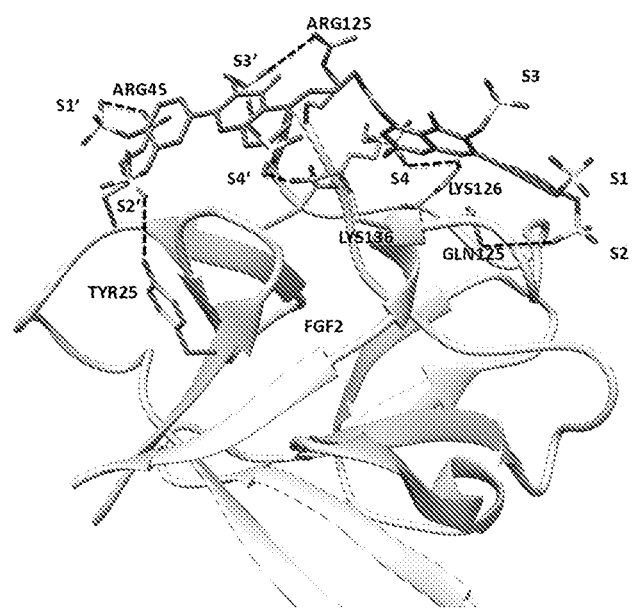
FIG. 2 shows G2.2 bound to FGF2. The binding site residues shown in stick representation. The position of sulfate groups in G2.2 are labeled.

MD simulations to assess the stability of G2.2-FGF2 complex indicated several key interactions were involved in its binding. These sulfates were located at positions S2, S4 and S3' on G2.2 (FIG. 2). These suggested that these sulfates cannot be replaced theoretically. Likewise, the sulfates at position S4', S1' and S2' were also found to interact with FGF2 but with lesser interaction occupancy. However, sulfates at positions S1 and S3, which faced distal sites from the binding region, were found to not be involved in high affinity binding of G2.2 to FGF2. This indicated suitability of these positions for chemical modifications with lipidic groups.

Figure 3:
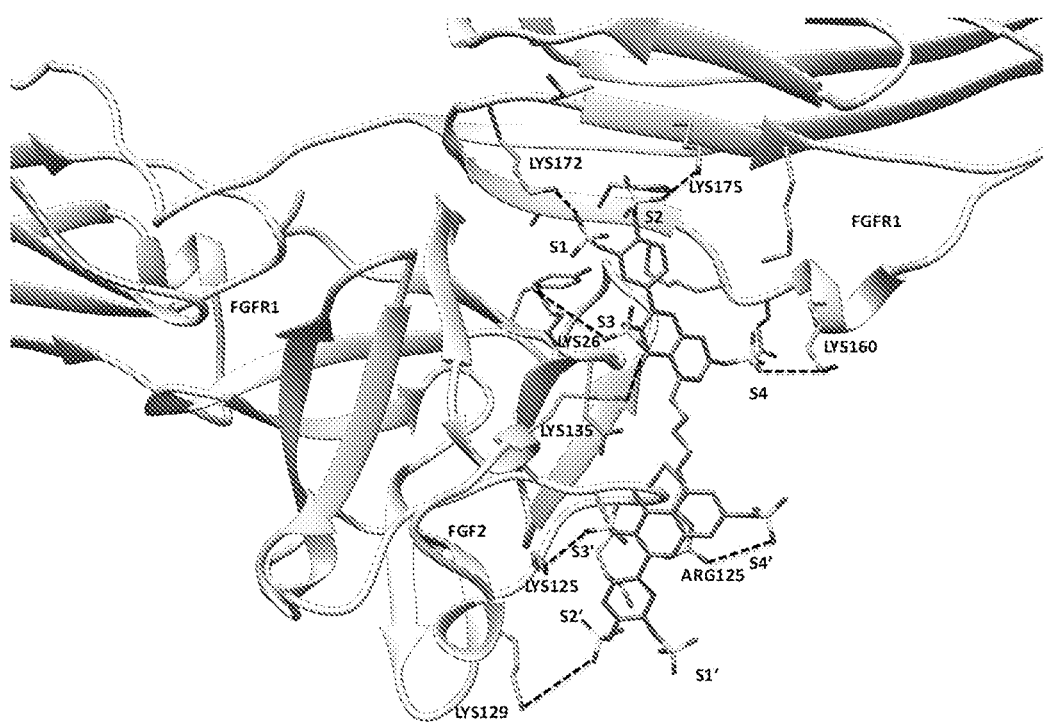
FIG. 3 shows FGF2-G2.2-FGFR1 complex with the binding site residues shown in stick representation. The position of sulfate groups in G2.2 are labeled.

Using MD we also assessed computationally whether G2.2 could form a stable ternary complex FGF2-FGFR1-G2.2 in presence of explicit water. The simulation trajectory showed that the sulfate groups at S1, S2' and S3' on G2.2 interact with Lys172, Lys129 and Lys125, respectively, and are of utmost importance in the formation of ternary complex (FIG. 3). Here, even though sulfates at S3 and S4 do not make any significant interactions with the either the protein or its receptor, these sulfates are present in the protein-protein interaction site, and addition of a lipophilic moiety at these positions would possibly disrupt protein-protein interactions owing to stearic bulk. More importantly, the MD studies indicated that two positions, S1' and S4', are neither involved in binding to the ternary complex nor are present in the protein-protein interacting site. Thus, these two sites were most probably the best possible modifications sites.

Figure 4:
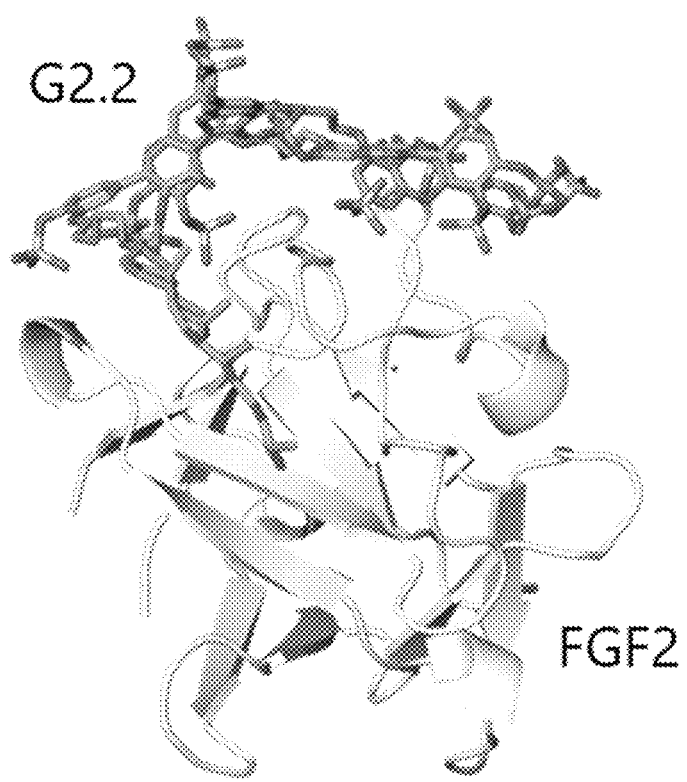
FIG. 4 shows the molecular docking of G2.2 and IIb in the heparin-biding region of FGF2 using GOLD (PDB ID: 1BFC).
Figure 5:
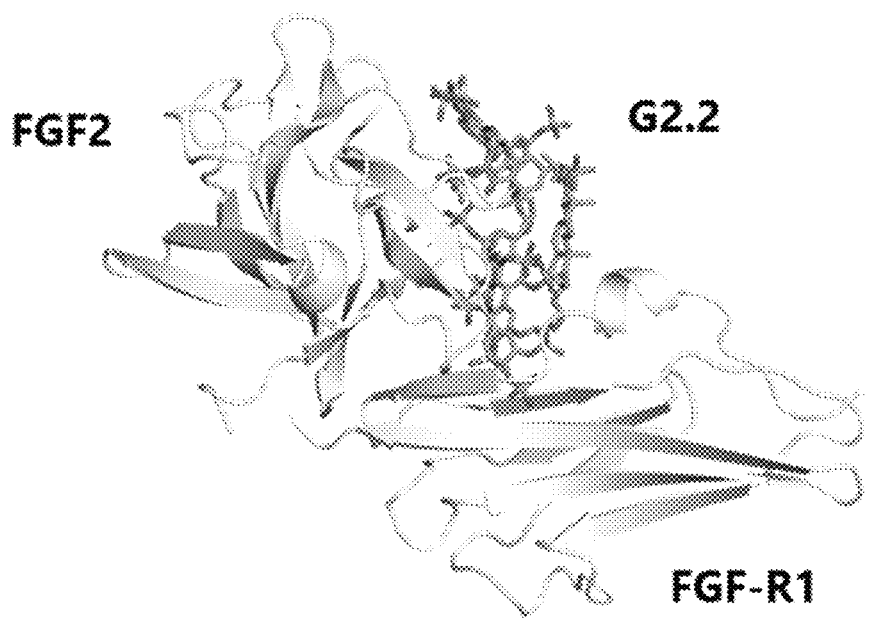
FIG. 5 shows the molecular docking of G2.2 and IIb in the heparin-binding region of FGF2-FGFR1 using GOLD (PDB ID: 1FQ9).

Based on these results we designed several analogs of G2.2 (FIG. 4) carrying cholesterol group attached to the 3'-position through linkers $L_1$ through $L_4$ (Formula I). The interaction of these analogs with FGF2 and FGFR1-FGF2 were studied in a manner identical to G2.2 discussed above. The GOLD scores for some of the most promising analogs are listed in Table 1. The results showed that the lipid-modified analogs had a lower score than that for G2.2 by ~25 units. For binding to FGF2, in general the lipidic analogs had a score better GOLD score than that for G2.2 suggesting their potential to exhibit higher CSC inhibitory activity. In addition, the key interactions and binding pose of FGF2-lipid analog complex (FIG. 5) were observed to be conserved. Thus, analysis of the docked poses indicated that the binding poses of G2.2 and lipidic analogs are very similar. Interestingly, the binding orientation of lipidic analogs tended to tilt ~20° suggesting that the addition of cholesterol places some sulfate groups in a slightly different orientation as compared to G2.2.

TABLE 1

GOLD scores of G2.2 and analogs complexes with FGF2 and FGF2-FGFR1.

| Compound | Gold Score | |
|---|---|---|
| | FGF2 | FGF2-FGFR1 |
| G2.2 | 109.8 | 144.7 |
| IIa | 112.3 | 125.3 |
| IIb | 110.6 | 136.3 |
| IIc | 117.6 | 117.6 |

Example 2. Anti-CSC Activity of Lipid Modified Analogs

The inhibitory potential of lipid-modified compounds of Formula I against CSCs was tested using a primary spheroids inhibition assay in various cancer cell lines including HT-29, RKO, HCT-116, LS1034, HC-15, WiDr, SW480, COLO205, NCI-H508, SW1116, LS174T, KM12 etc. Cells were grown both under monolayer and spheroid conditions as described in earlier work [Patel, N. J., et al. *ACS Chem. Biol.* 2014, 9, 1826-1833]. For primary sphere assay, cells were plated in non-treated, low adhesion, 96 wells plate at the concentration of 100 cells/100 µL/well in stem cell media (SCM) that consisted of DMEM:F12:AA, supplemented with 1×B27, 20 ng/mL epidermal growth factor, and 10 ng/mL fibroblast growth factor. After 4 h of incubation, vehicle (control) or G2.2 and its lipid analogs at the desired concentrations were added to each well (at least in triplicates for each sample). On day five, numbers of spheres ranging from 50 to 150 micrometers in diameter were counted using phase contrast microscope and percent inhibition was calculated compared to control. For monolayer assay, approximately $2.5 \times 10^3$ cells/100 µL/well were plated in 96-well tissue culture treated plate. After overnight incubation at 37° C. vehicle (control) or G2.2 was added at the desired concentration and the cells were further incubated for 60-72 h. At the end of the incubation, 10 µL of 5 mg mL$^{-1}$ MTT solution ((3-(4,5-dimethylthiazol-2-yl)-2,5-diphenyltetrazolium bromide, Sigma) made in phosphate buffered saline (PBS) (Gibco) was added to each well and incubated for minimum of 2 to 3 h until crystals formation was observed. Following this, 150 µL of 4 mM HCl (Sigma) in isopropanol solution was added dropwise to each well and the mixture was triturated until the crystals dissolve completely. Finally, the plate was placed on the spectrophotometer reader and read at 590 nm and growth inhibition was calculated as percent of control.

Figure 6:
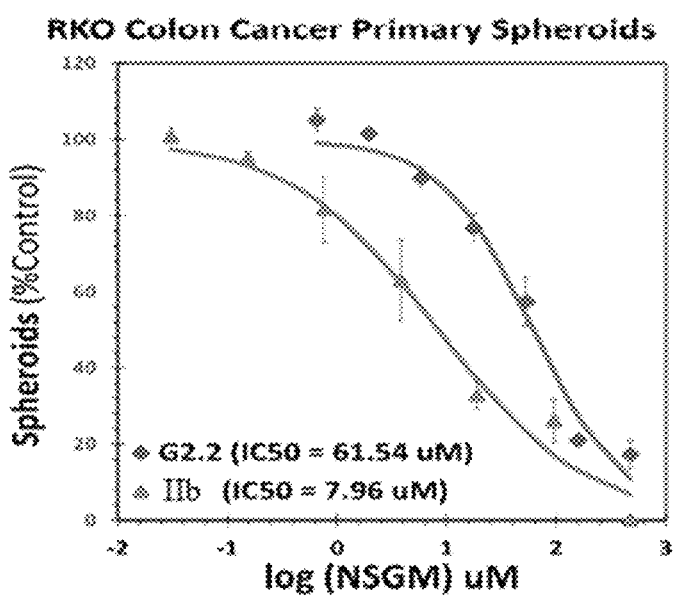
FIG. 6 is graph showing the dose-dependent inhibition of RKO colon spheroids by G2.2 and IIb.

Representative dose-response profiles of G2.2 and IIb are shown in FIG. 6. Table 2 shows $IC_{50}$ values calculated from dose-response profiles for G2.2, IIa, IIb and IIc for HT-29 spheroids. Cholesterol modification of G2.2 did result in an increase in anti-CSC inhibition potency, as expected, based on molecular modeling results. IIc was the most potent among the tested compounds with >35-fold increase in $IC_{50}$ from G2.2. Interestingly, a linear increase in inhibition potency with increase in the length of the linker was not observed, as one would have expected. IIa and IIc, with two- and eight-carbon linkers respectively, showed better inhibition of CSC spheroids when compared to IIb with a five-carbon linker. Further, all the lipid-modified analogs showed minimal cytotoxicity in monolayer culture (Table 2). As CSCs are significantly enriched in spheroids compared to monolayer controls, these findings suggest that like G2.2, the lipid-modified analogs preferentially inhibit CSCs.

TABLE 2

Inhibition potencies of lipid-modified G2.2 analogs against spheroid and monolayer growth of HT-29 cells.

| Compound | Spheroid $IC_{50}$ (µM) | Monolayer $IC_{50}$ (µM) | Selectivity Index |
|---|---|---|---|
| G2.2 | 29 ± 1 µM | >500 µM | >17 |
| IIa | 5.4 ± 1.3 µM | 393 ± 15% µM | 72 |
| IIb | 8.2 ± 1.5 µM | >500 µM | >60 |
| IIc | 0.8 ± 0.2 µM | 1079 ± 15% µM | 1348 |

Example 3. Pharmacokinetic (PK) Properties of Lipidic Analogs of G2.2

The animal protocol was approved by the Institutional Animal Care and Use Committee at VCU. Adult male Sprague-Dawley rats weighing 250-275 g were acclimatized for over 3 days with free access to standard rat diet and tap water. Animals were then placed on overnight fasting (i.e., without diet, but with free access to water) on a day before the PK studies. Each animal was anesthetized with an IP injection of urethane and an aliquot (0.1 mL) of blood was withdrawn as a prior-to-dosing or time 0 sample from the jugular vein with a use of 0.11 M sodium citrate (0.01 mL) as anti-coagulant. Rats (n=4 or 5) received G2.2 or IIb via IV injection or PO administration, while one animal received G2.2 via IP bolus injection. G2.2 and IIb were dissolved in sterile saline (0.1 mL IV and IP; 0.2 mLs PO). A series of blood aliquots (0.1 mL) were sampled from the jugular vein at different time points over 0 to 8 h. The blood samples were immediately centrifuged at 11,750 g for 3 min to yield the plasma samples, which were then stored at −70° C. At the conclusion of PK studies, all rats were euthanized by exsanguination under the surgical anesthesia.

The concentrations of G2.2 and lipid analogs in plasma were determined by the quantitative fluorimetry assay in which plasma samples were first diluted 2-fold (v/v) with 0.05 M PBS (pH 7.4), then an equal volume of methanol added and the mixture centrifuged at 11,750 g for 5 min. The supernatants were transferred to black 96 well-plates and the fluorescence at 528 nm (G2.2) or 460 nm (lipid analog) ($\lambda_{EX}$=340 nm) read using a microplate reader. Reference profiles, prepared for concentrations in the range of 0.5 and 50 μg/mL ($R^2$=0.98-0.99), were used to calculate plasma concentration at every time point.

Figure 7:
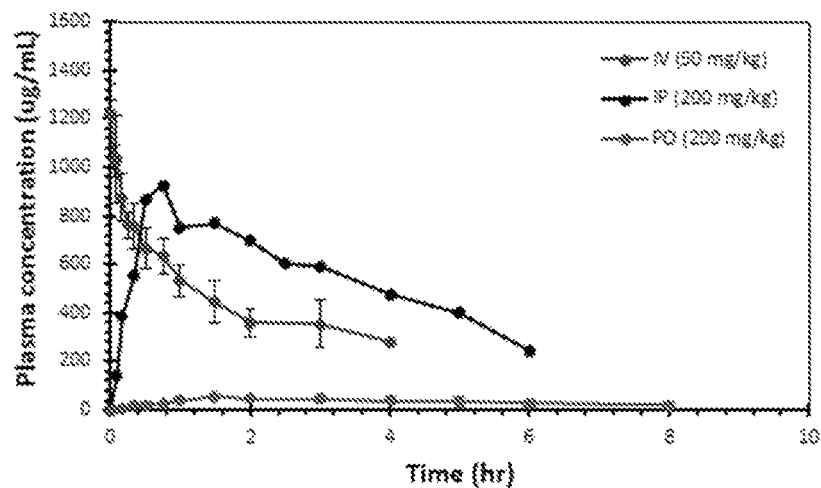
FIG. 7 illustrates the plasma concentration vs. time profile following IV bolus (50 mg/kg, N=5), IP bolus (200 mg/kg, N=1) and PO administration (200 mg/kg, N=4) of G2.2. Plasma concentration of G2.2 was measured using its fluorescence properties.

Following IV administration in rats, G2.2 showed a two-compartmental PK profile (FIG. 7). From this profile, we deduced that distribution phase was about 1.5 hours followed by an elimination phase with a terminal half-life of 4.4 hr. The PK profile was analyzed using conventional analysis. The parameters deduced included peak plasma concentration ($C_{max}$), the time required to reach $C_{max}$ ($T_{max}$), the plasma concentration-time curve ($AUC_{0-\infty}$), the terminal half-life ($t_{1/2}$), the apparent clearance (CL/F) and the apparent pseudo-steady state volume of distribution ($V_{pss}$/F). The absolute bioavailability (F) was deduced for G2.2, while relative bioavailability was deduced for lipid analogs.

The plasma PK profile following IP injection (FIG. 7) showed a $C_{max}$ of ~1350 μg/mL (925 μM) and a $T_{max}$ of 45 min. The absolute bioavailability was ~30%. This implies that sufficient G2.2 is likely to be present for some 6 in animals (assuming in vivo $IC_{50}$ of ~30 μM). Thus, the high levels administered through IV would be expected to exert efficacies in the in vivo xenograft mouse model.

Likewise, the plasma PK profile following PO administration at 200 mg/kg showed a $C_{max}$ of 81.2 μg/mL (55.6 μM) and a $T_{max}$ of 90 min, which is followed by a slow decline and elimination (FIG. 7, Table 3). The half-life of the elimination phase was 4.6 hr, which was comparable to the terminal half-life of 4.4 hr in the PK profile following IV injection. The absolute oral bioavailability of G2.2 was found to be ~3%. This implies that G2.2 has low oral bioavailability.

Figure 8:
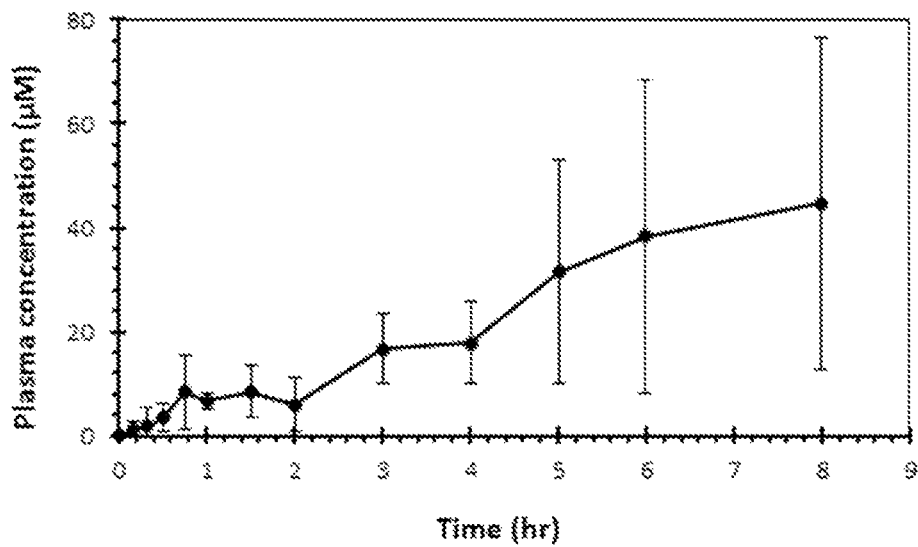
FIG. 8 illustrates the plasma concentration vs. time profile following PO administration of IIb at a nominal dose of 50 mg/kg in rats (N=4).

FIG. 8 shows the results obtained with a nominal dose of 50 mg/kg.

TABLE 3

PK parameters of G2.2 following IP and PO administrations.

| PK parameter | IP | PO |
| --- | --- | --- |
| $C_{max}$ (maximum plasma concentration) | 1350 μg/mL | 81 μg/mL |
| $T_{max}$ (time taken to reach $C_{max}$) | 45 min | 90 min |
| $t_{1/2}$ (terminal half-life) | 3 hr | 4.6 hr |
| $AUC_{0-\infty}$ (area under the plasma concentration v/s time curve) | 6398 μg · hr/mL | 584 μg · hr/mL |
| F (absolute bioavailability) | 30% | 3% |

In contrast, IIb showed a completely different pharmacokinetic profile following oral administration (FIG. 7). The plasma concentrations of IIb remained elevated up to 1 h, followed by a slight decrease for ~1 h. However, the plasma concentrations again started to rise up to 8 h. The profile may represent enterohepatic circulation (EHC) and reabsorption of IIb, as suggested for cholesterol PK. EHC is a physiologic process for bile salt recycling and some drugs undergo EHC and reappear in the gastrointestinal tract for reabsorption. EHC prolongs residence times of the drugs in the body, yielding longer half-lives; and results in multiple peaks in the plasma concentration vs. time profiles. At least 2 such peaks are seen in the profile of IIb above. It is now known that over 45 drugs on the market, including warfarin, morphine, erythromycin, and imipramine undergo EHC.

FIG. 8 shows the plasma concentration vs. time profile following PO administration of IIb at a nominal dose of 50 mg/kg in rats (N=4).

The bioavailability of IIb was calculated in relation to that of G2.2 by disregarding the phenomenon of EHC. The AUC values for G2.2 and IIb were calculated up to 8 h following PO administration using the trapezoid method and then the following equation was employed to calculate the relative bioavailability of IIb.

$$F_{rel} = 100 \cdot \frac{AUC_{G5C,PO} \cdot Dose_{G2.2,PO}}{AUC_{G2.2,PO} \cdot Dose_{G5C,PO}} = 333\%$$

Although this number appears to be small, it is clear that IIc absorption is far greater than that for G2.2 suggesting that cholesterol conjugation of G2.2 improved absorption properties.

Example 4. Effects on Coagulation

Glycosaminoglycans, especially heparin/HS, are known for their ability to inhibit the coagulation system. Because G2.2 and its lipid analogs are mimetics of GAGs, it is important to study their effects on the coagulation system. We measured the concentration of lipid-modified G2.2 analogs required to double the activated partial thromboplastin time (APTT; Table 4). The experiments were performed as described in earlier work [Henry, B. L., et al. *Blood Coag Fibrinol* 2009, 20, 27-34]. Briefly, a standard one-stage recalcification assay in a BBL Fibrosystem fibrometer (Becton-Dickinson, Sparles, MD) was used to measure clotting times in human plasma. A 10 μL aqueous solution of the lipidic analog at a desired concentration was mixed with 90 μL of citrated human plasma and 100 μL of prewarmed APTT reagent. After incubation for 4 min at 37° C., clotting was initiated by adding 100 μL of prewarmed 25 mM $CaCl_2$), and the time to clot was noted. The concentration of the analog required to double the clotting time was calculated from the clotting time versus concentration profile. In general, cholesterol modification of G2.2 increased its anticoagulation potency. Yet, studies indicate that the lipid modified analogs are not anticoagulant at their anti-cancer therapeutic values suggesting their safe use as anti-cancer agents (Table 4).

TABLE 4

Coagulation profile of lipid-modified G2.2 analogs

| Compounds | Concentration required to double APTT | $IC_{50}$ (HT-29 CSCs) | Safety Index |
| --- | --- | --- | --- |
| Enoxaparin | 2.5 μM | — | — |
| G2.2 | 640 μM | 29 ± 1 μM | 22-fold |
| IIa | 150 μM | 5.4 ± 1.3 μM | 28-fold |
| IIb | 48 μM | 8.2 ± 1.5 μM | 6-fold |
| IIc | 50 μM | 0.8 ± 0.2 μM | 63-fold |

Example 5. In Vivo Studies of Lipidic Analogs of G2.2

The in vivo therapeutic potential of IIb was performed in CSC-induced HT-29 xenografts model as described in an earlier work on G2.2 [Boothello, R., et al., *Mol. Cancer Ther.* 2019, 18, 51-56]. Briefly, the protocols were approved by the Animal Component of Research Protocol Committee at McGuire VA Medical Center, Richmond, VA Xenografts were generated by injecting $10^5$ CD133 hi/CXCR4hi (Dual hi) fluorescence-activated cell sorter (FACS) isolated HT29 cells suspended in 50% reduced growth factor Matrigel (BD Bioscience; in 50 μL sterile PBS) into the right flank of 6-week-old, female NCr nude mice (Taconic Farms) subcutaneously. Once the average tumor volume reached 50 mm³, animals were treated with FUOX (5-FU 25 mg/kg and oxaliplatin 2 mg/kg weekly for 3 weeks followed by the second randomization to vehicle, G2.2 (200 mg/kg) or IIb (100 mg/kg), 3 times a week×3 weeks) Mice were euthanized after the completion of treatment (an hour after the final injection) and ex vivo CSC phenotype studies performed.

Once the tumors reached 50 mm³, mice were randomized to either of the three groups (vehicle, 200 mg/kg G2.2, or 100 mg/kg IIb) and dosed i.p three times a week for three weeks. Tumor measurements on each animal were made 3 times a week with Vernier calipers, and tumor volume was calculated using the formula: $V=W^2 (L)/2$, where V is the volume in mm³, and W and L are the width and length in mm. At the end of the 3 weeks after treatment, appropriate numbers of animals were sacrificed in each group, and the tumor tissues were collected and processed (finely chopped and digested with 400 μg/mL Collagenase Type IV (STEM-CELL Technologies)). The remainder of animals were monitored till they reached predefined humane end-points. Animals were sacrificed per Institutional Animal Care and Use Committee—approved methods of euthanasia.

Figure 9:
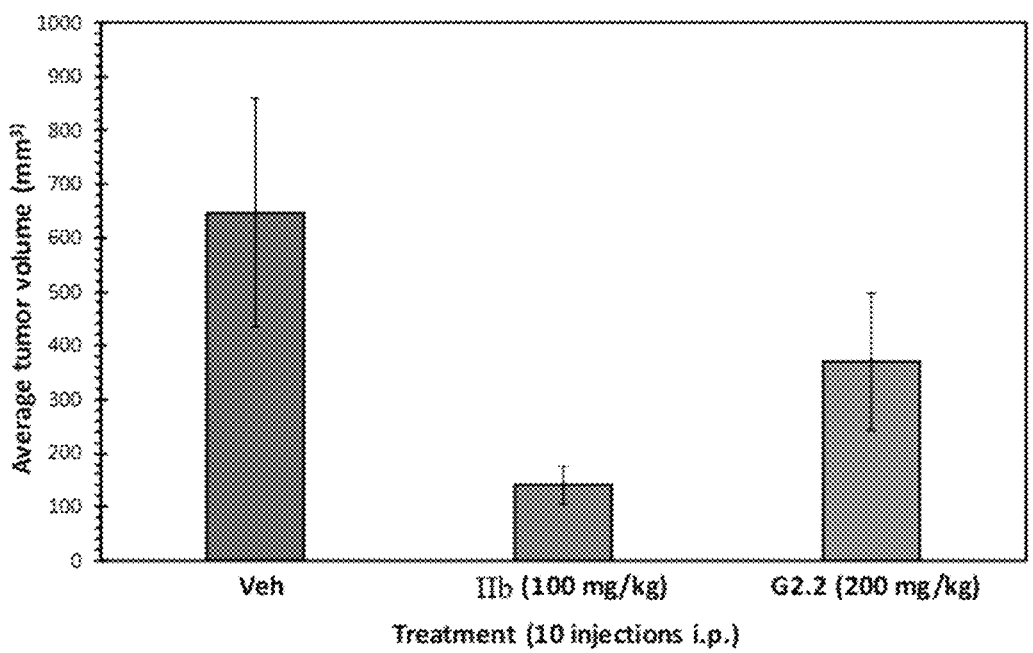
FIG. 9. IIb (100 mg/kg; i.p.) showed a significant reduction in tumor volume compared to vehicle treated mice. Additionally, the reduction in tumor volume was more than what was observed with G2.2 (200 mg/kg; i.p.).
Figure 10:
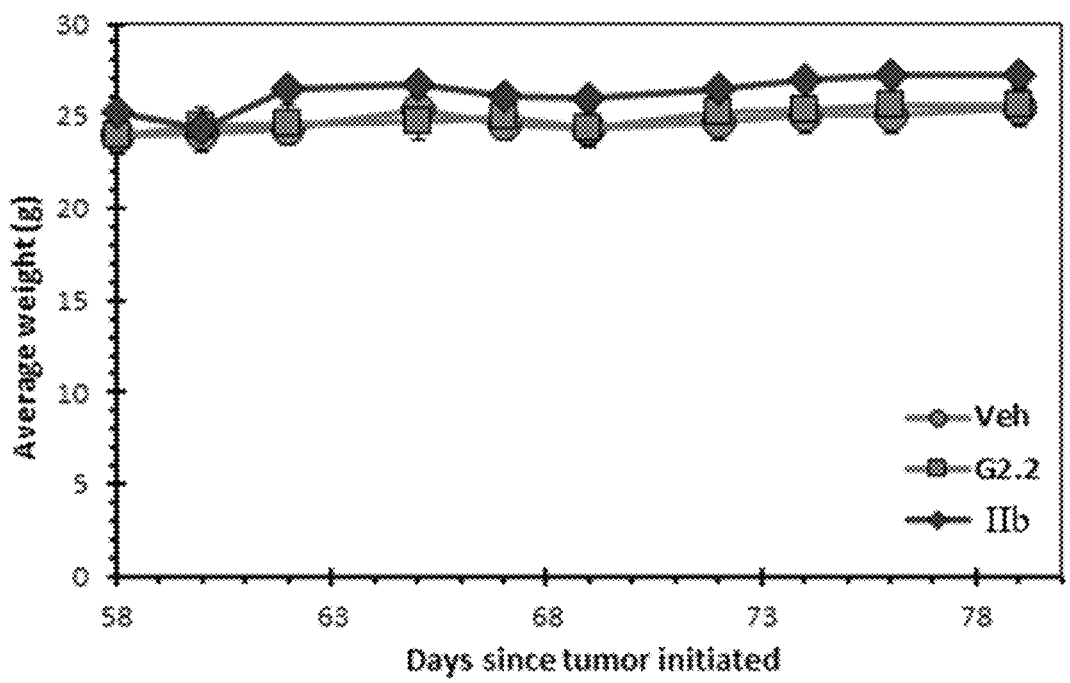
FIG. 10. IIb showed no gross toxicity, assessed with respect to body weight, when injected i.p. to nude mice.
Figure 11:
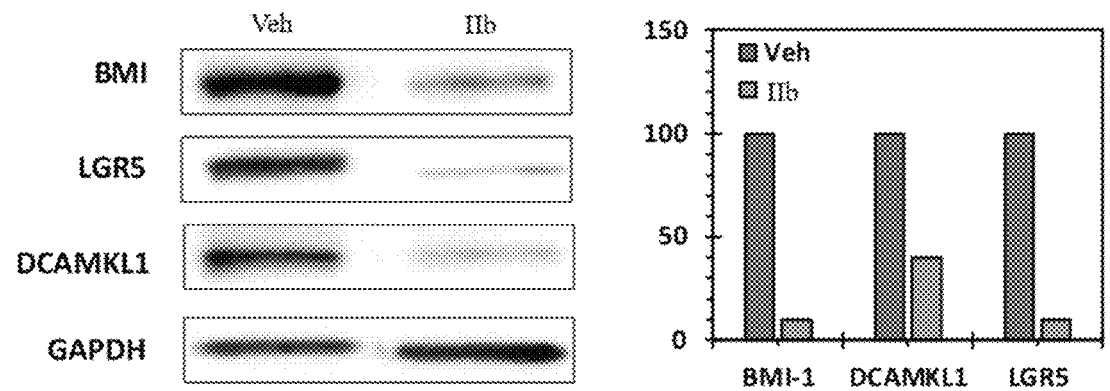
FIG. 11. IIb treated mice show a reduction in CSC markers (BMI-1, DVCMKL1, and LGR5) compared to vehicle treated mice as observed through western blot analysis of mice xenografts.
Figure 12:
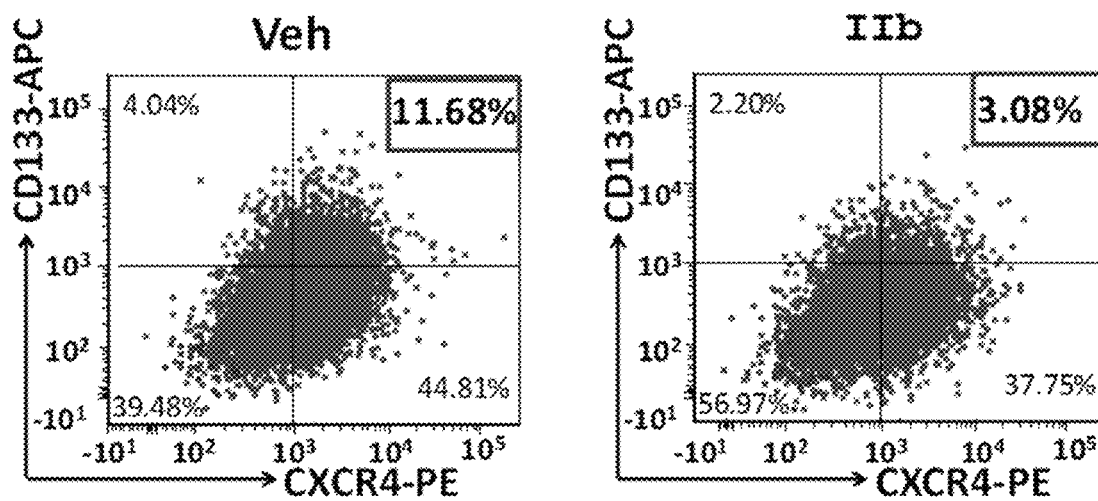
FIG. 12. IIb-treated xenografts show several-fold reduction in LGR5+ cells in comparison to vehicle-treated xenografts.

Intriguingly, the tumor volumes at the end of the treatment displayed a robust >80% decrease in the IIb (100 mg/kg)-treated mice compared with vehicle controls (FIG. 9). Mice dosed with IIb did not show any gross toxic effects, especially with respect to animal weight (FIG. 10). These effects of IIb appear to be >2-fold compared to G2.2 (200 mg/kg), despite administrating half the dose. In line with significant tumor volume changes, IIb treatment resulted in a robust reduction in a complement of CSC markers DCLK1 and LGR5) as well as self-renewal factor (BMI-1) as seen in FIG. 11. Additionally, there was approximately 3.9-fold reduction in the numbers of LGR5+ cells in IIb-treated xenografts compared with vehicle controls (FIG. 12).

Figure 13:
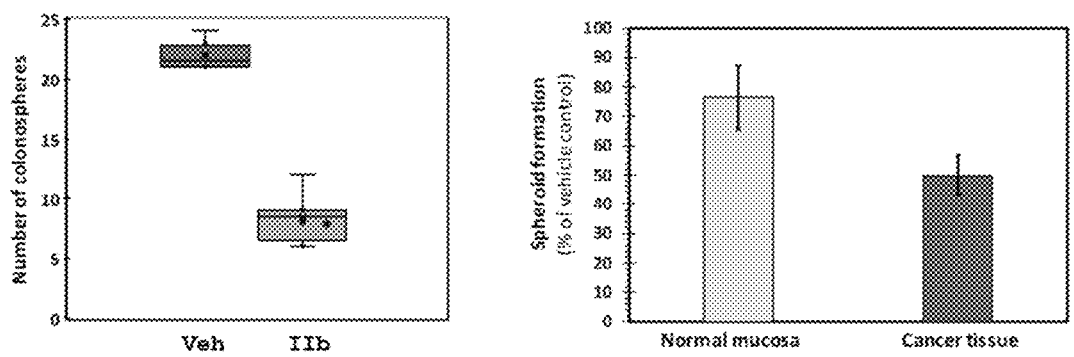
FIG. 13 shows a flow cytometry analysis of mice xenografts showing a reduction in CSC markers in IIb treated mice.

We also utilized our earlier observation that CSCs/progenitors are enhanced several-fold in spheroid culture and assessed the xenografts-derived cells for retention of tertiary spheroid growth inhibition profiles to distinguish between non self-renewing progenitors and self-renewing CSCs ex vivo. Indeed, cells derived from IIb-treated xenografts showed a robust 2.6-fold decrease in 3° spheroid formation, measured a week after the last dose of IIb, compared with vehicle controls (FIG. 13).

Overall, the in vivo studies show that IIb is significantly more potent (~4-fold) than G2.2. More importantly, when IIb (5 μM) was tested to inhibit spheroid growth formation in both normal and cancerous colon tissue obtained from a patient, it significantly inhibited cancerous tissue-derived primary human spheroids without any effect on the normal tissue.

Example 6. Molecular Design of Lipidic Analogs of G2.2

The crystal structure coordinates of FGF2 and FGF2-FGFR1 complex were retrieved from the PDB database (ID: 1BFC, 2.2 Å resolution and ID: 1FQ9, 3.0 Å resolution, respectively) and prepared for molecular modeling studies using the protein preparation tool in Tripos Sybyl-X v2.2 (www.tripos.com/sybyl). We followed the procedure described in detail in Nagarajan et al. (Nagarajan, B., et al., *PLoS One* 2017, 12, e0171619). Briefly, hydrogen atoms were added and minimized with fixed heavy-atom coordinates using the Tripos force field. The potential site of binding of G2.2 and lipidic analogs was identified by using the centroid of the heparin sequence in the complexes [Faham, S., et al., *Science* 1996, 271, 1116-1120; Schlessinger, J., et al., *Mol. Cell* 2000, 6, 743-750]. An 18 Å docking radius was used to define the potential binding site. G2.2 and its analogs were optimized using Sybyl, and were docked onto the three proteins FGF2, FGFR1, FGFR1-FGF2 using GOLD v5.2. The docked poses were scored and the top two docked poses from each run were retained for analysis of consistency of binding. Details on the fitness of binding was calculated from the hydrogen bond and van der Waals interactions between the protein and G2.2/analogs.

To assess the fitness of the docked structures, G2.2 complexes with FGF2, FGFR1, and FGFR1-FGF2 obtained from GOLD were prepared for molecular dynamics (MD) according to the procedure described in details by Nagarajan et al. AMBER-ff99SB force field was utilized for the protein receptors, the overall charge was neutralized and then the complexes placed in the center of a TIP3P cuboid water box with minimum distance of 12 Å between the box wall to any atom of the complex. MD simulations were performed using AMBER14.

Examples 7-13 show the synthesis steps to produce compounds having Formulas IIa, IIb and IIc.

Example 7

Procedure for the Tosylation of Cholesterol

To a solution of cholesterol (1 eq.) in DCM, 4-toluene-sulfonylchloride (1.5 eq.) was added and stirred for 2 min. This was followed by the addition of 1.5 eq. of triethylamine and 0.05 eq. of 4-dimethylaminopyridine. The mixture was allowed to stir at room temperature for 12 h. and monitored continuously using TLC. After the reaction completion as indicated by TLC, the reaction mixture was diluted with a mixture of dichloromethane/H$_2$O. The organic layer was separated, and the aqueous phase was further extracted with dichloromethane. The organic layer was then washed with saturated NaCl solution. The three organic layers were combined, dried over anhydrous Na$_2$SO$_4$, and concentrated under reduced pressure to afford the crude intermediate which was further purified using flash chromatography on silica gel. The pure intermediate, 1a, was obtained as white solid in yields of 90-95%. $^1$H NMR (400 MHz, CDCl$_3$) δ 7.72 (d, J=8.28 Hz, 2H), 7.25 (d, J=8.12 Hz, 2H), 5.23-5.22 (m, 1H), 4.30-4.21 (m, 1H), 2.37 (s, 3H), 2.36-2.31 (m, 1H), 2.36-2.31 (m, 1H), 2.24-2.16 (m, 1H), 1.97-1.83 (m, 2H), 1.80-1.69 (m, 3H), 1.68-1.56 (m, 1H), 1.51-1.14 (m, 10H), 1.10-0.88 (m, 12H), 0.85-0.77 (m, 10H), 0.59 (s, 3H).

Example 8

General Procedure for the Attachment of Linker to Cholesterol Tosylate

To a solution of cholesterol tosylate (1a) in dry dioxane was added was dry ethylene glycol or 1,5-pentanediol or 1,8-octanediol or diethylene glycol or triethylene glycol (25 eq.). The mixture was refluxed overnight at 110 C. The solution was allowed to cool and the solvent was removed under vacuum. The resulting residue was dissolved in ethyl acetate and washed with NaHCO$_3$, water and brine. The organic layer was dried using anhydrous Na$_2$CO$_3$, dried under vacuum and purified using flash chromatography to afford the respective compounds, 1b-3b, in 50-70% yield.

1b. $^1$H NMR (400 MHz, acetone-d$_6$) δ 5.36-5.32 (m, 1H), 3.62-3.54 (m, 6H), 3.54-3.50 (m, 2H), 3.21-3.11 (m, 1H), 2.39-2.32 (m, 1H), 2.18-2.09 (m, 1H), 2.01-1.81 (m, 4H), 1.66-1.24 (m, 11H), 1.23-1.03 (m, 8H), 1.01 (s, 3H), 0.95 (d, J=6.56 Hz, 3H), 1.51-1.14 (dd, J=2.64 Hz, 6H), 0.72 (s, 3H). MS (ESI) calculated for $C_{29}H_{50}O_2$, found for [(M+Na)]$^+$, m/z 453.71, found for [(M+Na)]$^+$, 453.69.

2b. $^1$H NMR (400 MHz, CDCl$_3$) δ 5.35-5.32 (m, 1H), 3.70 (s, 1H), 3.68-3.61 (m, 2H), 3.49-3.43 (m, 2H), 3.13-3.09 (m, 1H), 2.38-2.30 (m, 1H), 2.24-2.12 (m, 1H), 2.01-1.77 (m, 4H), 1.65-1.29 (m, 18H), 1.37-1.03 (m, 8H), 1.00 (s, 4H), 0.92 (d, J=6.56 Hz, 4H), 0.86 (dd, J=2.64 Hz, 6H), 0.67 (s, 3H). MS (ESI) calculated for $C_{32}H_{56}O_2$, [(M+H)]$^+$, m/z 473.44 found for [(M+H)]$^+$, 473.47.

3b. $^1$H NMR (400 MHz, CDCl$_3$) δ 5.35-5.32 (m, 1H), 3.64 (t, J=6.22 Hz, 2H), 3.49-3.43 (m, 2H), 3.17-3.09 (m, 1H), 2.39-2.32 (m, 1H), 2.24-2.14 (m, 1H), 2.07-1.77 (m, 5H), 1.63-1.29 (m, 25H), 1.29-0.97 (m, 16H), 0.93-0.91 (m, 3H), 0.89-0.85 (m, 6H), 0.68 (s, 3H). MS (ESI) calculated for $C_{35}H_{62}O_2$, [(M+Na)]$^+$, m/z 537.46, found for [(M+Na)]$^+$, 537.60.

Example 9

General Procedure for the Tosylation of Intermediates 1b-3b

To a solution of 1b or 2b or 3b in DCM were added triethylamine (1.5 eq.), 4-dimethylaminopyridine (0.05 eq.) and 4-toluenesulfonylchloride (1.5 eq.) under an atmosphere of nitrogen. The reaction was stirred overnight at room temperature and washed with dilute HCl, saturated brine and water. The organic layer was dried over Na$_2$SO$_4$, concentrated under vacuum and purified using flash chromatography to obtain compounds 1c-3c in 90-95% yield.

1c. $^1$H NMR (400 MHz, CDCl$_3$) δ 7.80 (d, J=8.28 Hz, 2H), 7.33 (d, J=8.04 Hz, 2H), 5.35-5.32 (m, 1H), 4.14 (t, J=4.96 Hz, 2H), 3.64 (t, J=4.96 Hz, 2H), 3.14-3.02 (m, 1H), 2.44 (s, 3H), 2.35-2.28 (m, 1H), 2.14-1.93 (m, 3H), 1.89-1.73 (m, 3H), 1.62-1.19 (m, 14H), 1.19-1.03 (m, 6H), 0.96-0.82 (m, 14H), 0.67 (s, 3H). MS (ESI) calculated for $C_{36}H_{56}O_4S$, [(M+Na)]$^+$, m/z 607.3793, found for [(M+Na)]$^+$, 607.2901.

2c. $^1$H NMR (400 MHz, CDCl$_3$) δ 7.78 (d, J=8.28 Hz, 2H), 7.34 (d, J=8.04 Hz, 2H), 5.35-5.32 (m, 1H), 4.02 (t, J=6.52 Hz, 2H), 3.41-3.35 (m, 2H), 3.13-3.03 (m, 1H), 2.44 (s, 3H), 2.35-2.28 (m, 1H), 2.20-2.10 (m, 1H), 2.05-1.93 (m, 2H), 1.89-1.78 (m, 3H), 1.70-1.62 (m, 2H), 1.59-1.22 (m, 16H), 1.22-0.94 (m, 12H), 0.93-0.82 (m, 9H), 0.67 (s, 3H). MS (ESI) calculated for $C_{39}H_{62}O_4S$, [(M+Na)]$^+$, m/z 649.43, found for [(M+Na)]$^+$, 649.29.

3c. $^1$H NMR (400 MHz, CDCl$_3$) δ 7.79 (d, J=8.32 Hz, 2H), 7.34 (d, J=8.08 Hz, 2H), 5.35-5.32 (m, 1H), 4.01 (t, J=6.52 Hz, 2H), 3.46-3.39 (m, 2H), 3.14-3.07 (m, 1H), 2.44 (s, 3H), 2.38-2.31 (m, 1H), 2.22-2.13 (m, 1H), 2.05-1.77 (m, 4H), 1.66-1.20 (m, 24H), 1.19-0.94 (m, 12H), 0.93-0.91 (m, 4H), 0.89-0.83 (m, 6H), 0.68 (s, 3H). MS (ESI) calculated for $C_{42}H_{68}O_4S$, [(M+Na)]$^+$, m/z 692.05, found for [(M+Na)]$^+$, 691.53.

Example 10

General Procedure for Attachment of Tosylated Lipids (1c-3c) to Triprotected Quercetin To a solution of triprotected quercetin (1 eq.) in anhydrous DMF were added K$_2$CO$_3$ (1.5 eq.) and 1c, 2c or 3c (1 eq.). The solution was stirred under an atmosphere of nitrogen for 48 hours. The solution was quenched with dilute HCl and extracted with ethyl acetate. The organic layer was washed with saturated brine and water and dried over anhydrous Na$_2$SO$_4$. The solvent was removed using vacuum and the product purified using flash chromatography to obtain pure compounds, 1d-3d, in 40-70% yield.

1d. $^1$H NMR (400 MHz, CDCl$_3$) δ 12.53 (s, 1H), 7.69-7.62 (m, 2H), 7.23 (d, J=8.52 Hz, 2H), 6.61 (d, J=2.12 Hz, 1H), 6.46 (d, J=2.12 Hz, 1H), 5.37-5.33 (m, 1H), 5.28 (s, 2H), 5.23 (s, 2H), 5.17 (s, 2H), 4.24 (t, J=5.20 Hz, 2H), 3.90 (t, J=5.22 Hz, 2H), 3.53 (s, 3H), 3.50 (s, 3H), 3.33-3.26 (m, 1H), 3.22 (s, 3H), 2.44-2.37 (m, 1H), 2.29-2.19 (m, 1H), 2.02-1.78 (m, 4H), 1.63-1.30 (m, 14H), 1.20-0.95 (m, 14H), 0.91 (d, J=6.52 Hz, 4H), 0.87 (dd, J=2.77 Hz, 6H), 0.68 (s, 3H). MS (ESI) calculated for $C_{50}H_{70}O_{11}$, [(M+H)]$^+$, m/z 847.49, found for [(M+H)]$^+$, 847.37.

2d. $^1$H NMR (400 MHz, CDCl$_3$) δ 12.53 (s, 1H), 7.66-7.59 (m, 2H), 7.22 (d, J=8.52 Hz, 2H), 6.61 (d, J=2.16 Hz, 1H), 6.46 (d, J=2.16 Hz, 1H), 5.35-5.32 (m, 1H), 5.28 (s, 2H), 5.23 (s, 2H), 5.17 (s, 2H), 3.54 (s, 3H), 3.49 (s, 3H), 3.22 (s, 3H), 3.17-3.08 (m, 1H), 2.39-2.30 (m, 1H), 2.23-2.14 (m, 1H), 2.03-1.78 (m, 8H), 1.70-1.30 (m, 18H), 1.25-0.95 (m, 12H), 0.91 (d, J=6.52 Hz, 3H), 0.87 (dd, J=2.77 Hz, 6H) 0.68 (s, 3H). MS (ESI) calculated for $C_{53}H_{76}O_{11}$, [(M+H)]$^+$, m/z 889.54, found for [(M+H)]$^+$, 889.32.

3d. $^1$H NMR (400 MHz, CDCl$_3$) δ 12.53 (s, 1H), 7.66-7.59 (m, 2H), 7.24 (d, J=8.52 Hz, 2H), 6.61 (d, J=2.16 Hz, 1H), 6.46 (d, J=2.16 Hz, 1H), 5.36-5.33 (m, 1H), 5.28 (s, 2H), 5.23 (s, 2H), 5.17 (s, 2H), 3.53 (s, 3H), 3.49 (s, 3H), 3.48-3.42 (m, 2H), 3.22 (s, 3H), 3.16-3.08 (m, 1H), 2.39-2.30 (m, 1H), 2.23-2.14 (m, 1H), 2.03-1.78 (m, 7H), 1.63-1.26 (m, 23H), 1.28-0.94 (m, 12H), 0.91 (d, J=6.52 Hz, 3H), 0.87 (dd, J=2.77 Hz, 6H), 0.67 (s, 3H). MS (ESI) calculated for $C_{56}H_{82}O_{11}$, [(M+Na)]$^+$, m/z 953.57, found for [(M+Na)]$^+$, 953.65.

Example 11

General Procedure for Dimerization of Lipid Modified Analogs

To a solution of 1d, 2d or 3d (1 eq.) in anhydrous DMF were added K$_2$CO$_3$ (1.5 eq.) and 2-(3,4-bis(methoxymethoxy)phenyl)-5-(3-bromopropoxy)-3,7-bis(methoxymethoxy)-4H-chromen-4-one (1 eq.) and the reaction stirred under an atmosphere of nitrogen with heating at 60 C for 48 hours. The reaction was quenched with diluted HCl and extracted with ethyl acetate. The organic layer was washed with saturated brine and water, dried under Na$_2$CO$_3$ and the solvent removed by vacuum. The product was purified using flash chromatography to obtain the pure compounds in yields of 50-60%.

2e. $^1$H NMR (400 MHz, CDCl$_3$) δ 7.87 (d, J=2.05 Hz, 1H), 7.69-7.64 (m, 2H), 7.57-7.54 (m, 1H), 7.25-7.17 (m, 2H), 6.66-6.62 (m, 2H), 6.56-6.52 (m, 2H), 5.35-5.32 (m, 1H), 5.30 (s, 2H), 5.28 (s, 2H), 5.26 (s, 2H), 5.21 (s, 2H), 5.18 (s, 2H), 5.17 (s, 2H), 4.46-4.42 (m, 4H), 3.54 (s, 3H), 3.54-3.51 (m, 6H), 3.48 (s, 6H), 3.20 (s, 3H), 3.17 (s, 3H), 2.56-2.47 (m, 2H), 2.39-2.30 (m, 1H), 2.23-2.14 (m, 1H), 2.03-1.78 (m, 7H), 1.70-1.29 (m, 22H), 1.21-1.03 (m, 7H), 0.99 (s, 6H), 0.91 (d, J=6.52 Hz, 3H), 0.87 (dd, J=2.77 Hz, 6H), 0.68 (s, 3H). MS (ESI) calculated for $C_{79}H_{100}O_{22}$, [(M+H)]$^+$, m/z 1407.72, found for [(M+H)]$^+$, 1407.63.

3e. $^1$H NMR (400 MHz, CDCl$_3$) δ 7.88 (d, J=2.05 Hz, 1H), 7.69-7.63 (m, 2H), 7.58-7.55 (m, 1H), 7.25-7.17 (m, 2H), 6.66-6.62 (m, 2H), 6.56-6.52 (m, 2H), 5.35-5.32 (m, 1H), 5.29 (s, 2H), 5.28 (s, 2H), 5.26 (s, 2H), 5.21 (s, 2H), 5.18 (s, 2H), 5.16 (s, 2H), 4.46-4.42 (m, 4H), 4.07 (t, J=2.05 Hz, 2H), 3.54-3.51 (m, 9H), 3.47 (s, 6H), 3.19 (s, 3H), 3.16 (s, 3H), 2.56-2.47 (m, 2H), 2.39-2.30 (m, 1H), 2.23-2.14 (m, 1H), 2.05-1.75 (m, 6H), 1.70-1.28 (m, 24H), 1.25 (s, 6H), 1.19-1.01 (m, 6H), 0.99 (s, 4H), 0.91 (d, J=6.52 Hz, 3H), 0.87 (dd, J=2.77 Hz, 6H), 0.68 (s, 3H).

Example 12

General Procedure for Deprotection of Lipid Modified Analogs

The MOM groups of 1e-3e were completely deprotected by PTSA (4 eq./OH) in methanol. Briefly, MOM-protected molecule was dissolved in about 2 mL of dry DCM, and methanol was subsequently added. PTSA was added and the solution was refluxed for 12-24 hours and deprotection was monitored using MS until the reaction reached completion. Ethyl acetate (25 mL) was added to precipitate the polyphenol product from the reaction mixture. The precipitate was filtered, washed with excess ethyl acetate to remove the excess p-toluenesulfonic acid and dried to obtain pure polyphenols, 1f-3f, as yellow to orange solid which were used in subsequent reactions without further purification.

1f. MS (ESI) calculated for $C_{62}H_{72}O_{15}$, $[(M+H)]^+$, m/z 1057.49, found for $[(M+H)]^+$, 1057.38.

2f. $^1$H NMR (400 MHz, CDCl$_3$) δ 10.64 (d, J=11.16 Hz, 2H), 9.56-9.34 (m, 2H), 9.20 (bs, 1H), 8.71 (d, J=19.15 Hz, 2H), 7.73 (d, J=1.76 Hz, 1H), 7.57-7.54 (m, 2H), 7.47 (dd, J=8.53 Hz, J=2.31 Hz, 1H), 6.92 (d, J=8.48 Hz, 1H), 6.85 (d, J=8.48 Hz, 1H), 6.49 (d, J=1.84 Hz, 1H), 6.44 (d, J=1.88 Hz, 1H), 6.38-6.35 (m, 2H), 5.20 (bs, 1H), 4.34 (s, 4H), 4.10-4.00 (m, 2H), 3.46-3.37 (m, 2H), 3.08-2.97 (m, 1H), 2.37-2.20 (m, 3H), 1.95-1.63 (m, 8H), 1.60-1.21 (m, 14H), 1.15-0.92 (m, 8H), 0.91-0.72 (m, 15H), 0.59 (s, 3H). MS (ESI) calculated for $C_{65}H_{78}O_{15}$, $[(M+H)]^+$, m/z 1099.54, found for $[(M+H)]^+$, 1099.49.

3f. $^1$H NMR (400 MHz, CDCl$_3$) δ 10.66 (d, J=9.73 Hz, 2H), 9.51-9.37 (m, 2H), 9.22 (bs, 1H), 8.75 (d, J=13.08 Hz, 2H), 7.71 (d, J=1.96 Hz, 1H), 7.66-7.59 (m, 2H), 7.47 (dd, J=8.71 Hz, J=2.40 Hz, 1H), 6.94 (d, J=8.48 Hz, 1H), 6.85 (d, J=8.52 Hz, 1H), 6.50 (d, J=1.96 Hz, 1H), 6.44 (d, J=1.96 Hz, 1H), 6.38-6.35 (m, 2H), 5.21 (bs, 1H), 4.35 (t, J=5.02 Hz, 4H), 4.00-4.12 (t, J=6.60 Hz, 2H), 3.08-2.96 (m, 1H), 2.37-2.20 (m, 3H), 2.06-1.97 (m, 1H), 1.92-1.64 (m, 7H), 1.54-1.20 (m, 20H), 1.14-0.74 (m, 23), 0.59 (s, 3H). MS (ESI) calculated for $C_{68}H_{84}O_{15}$, $[(M+H)]^+$, m/z 1141.58, found for $[(M+H)]^+$, 1141.72.

Example 13

General Procedure for Sulfation of Lipid Modified Analogs

Sulfation of polyphenols, 1f-3f, was performed using microwave-assisted chemical protocol. Briefly, to a stirred solution of polyphenol in anhydrous CH$_3$CN (~3 mL) at room temperature, Et$_3$N (10 eq/—OH group) and SO$_3$/Me$_3$N complex (6 eq/—OH) were added. The reaction vessel was sealed and microwaved (CEM Discover, Cary, NC) for 7 hrs at 90° C. The reaction mixture was cooled and concentrated in vacuo at temperature <30° C. The reaction mixture was then purified on Combiflash RF system using CH$_2$Cl$_2$/CH$_3$OH mobile system (6:4) to obtain the persulfated molecules. The fractions containing the desired molecule were pooled together, concentrated in vacuo, and re-loaded onto a SP Sephadex C-25 column for sodium exchange. Desired fractions containing sodium salts of the per-sulfated molecules were pooled, concentrated in vacuo, and lyophilized to obtain a fluffy white powder.

IIa. $^1$H NMR (400 MHz, DMSO-d$_6$) δ 8.07 (d, J=2.32 Hz, 1H), 8.03-7.98 (m, 1H), 7.95 (s, 1H), 7.62-7.54 (m, 3H), 7.07 (d, J=1.84 Hz, 1H), 6.99 (d, J=1.88 Hz, 1H), 6.70 (dd, J=15.12 Hz, J=1.92 Hz, 1H), 5.28 (bs, 1H), 4.32-4.21 (m, 4H), 4.12-4.07 (m, 2H), 3.73-3.65 (m, 2H), 3.19-3.10 (m, 1H), 2.37-2.20 (m, 3H), 2.14-2.00 (m, 1H), 1.95-1.66 (m, 4H), 1.53-0.86 (m, 24H), 0.82 (d, J=6.33 Hz, 4H), 0.78 (dd, J=6.60 Hz, J=1.82 Hz, 7H), 0.58 (s, 3H). $^{13}$C NMR (100 MHz, DMSO-d$_6$) δ 172.91, 159.07, 158.29, 157.02, 153.28, 152.96, 148.41, 146.45, 152.21, 142.93, 140.56, 135.32, 124.52, 123.60, 121.04, 119.86, 109.58, 78.66, 56.17, 55.56, 49.56, 41.85, 36.66, 35.64, 35.16, 31.43, 31.36, 28.00, 27.76, 27.36, 23.85, 23.16, 22.64, 22.37, 20.59, 19.06, 18.54, 11.87. MS (ESI) calculated for $C_{62}H_{65}Na_7O_{36}S_7$, $[(M-2NaH)]^{2-}$, m/z 862.04, found for $[(M+H)]^+$, 862.28.

IIb. $^1$H NMR (400 MHz, DMSO-d$_6$) δ 8.07 (d, J=2.24 Hz, 1H), 8.03-7.91 (m, 2H), 7.62-7.52 (m, 3H), 7.07 (d, J=1.80 Hz, 1H), 6.99 (d, J=1.76 Hz, 1H), 6.74-6.65 (m, 2H), 5.23 (bs, 1H), 4.32-4.21 (m, 4H), 3.98 (t, J=6.24 Hz, 2H), 3.42-3.32 (m, 2H), 3.07-2.93 (m, 1H), 2.36-2.20 (m, 3H), 2.07-1.63 (m, 6H), 1.53-0.80 (m, 32H), 0.77 (dd, J=6.60 Hz, J=1.82 Hz, 7H), 0.58 (s, 3H). $^{13}$C NMR (100 MHz, DMSO-d$_6$) δ 172.98, 159.08, 158.33, 157.06, 153.31, 153.08, 148.75, 146.46, 145.19, 142.94, 140.65, 135.36, 135.32, 124.56, 123.65, 120.90, 120.44, 119.95, 119.52, 118.89, 114.70, 109.59, 100.63, 99.45, 99.22, 78.15, 68.50, 67.02, 66.09, 56.17, 55.57, 49.59, 41.84, 36.71, 36.30, 35.63, 35.16, 31.41, 31.35, 29.44, 28.70, 28.12, 27.75, 27.35, 23.83, 23.17, 22.63, 22.37, 22.32, 20.57, 19.06, 18.54, 11.65. MS (ESI) calculated for $C_{65}H_{71}Na_7O_{36}S_7$, $[(M-2NaH)]^{2-}$, m/z 883.06, found for $[(M+H)]^+$, 883.13.

IIc. $^1$H NMR (400 MHz, DMSO-d$_6$) δ 8.08 (d, J=2.28 Hz, 1H), 8.03-7.90 (m, 2H), 7.62-7.54 (m, 3H), 7.07 (d, J=1.88 Hz, 1H), 6.99 (d, J=1.84 Hz, 1H), 6.74-6.65 (m, 2H), 5.23 (bs, 1H), 4.32-4.21 (m, 4H), 4.03-3.91 (m, 2H), 3.04-2.93 (m, 1H), 2.37-2.20 (m, 3H), 2.05-1.58 (m, 8H), 1.53-0.96 (m, 25H), 0.95-0.84 (m, 7H), 0.82 (d, J=7.14 Hz, 4H), 0.77 (dd, J=6.60 Hz, J=1.82 Hz, 7H), 0.58 (s, 3H). $^{13}$C NMR (100 MHz, DMSO-d$_6$) δ 173.00, 159.08, 158.33, 157.01, 153.31, 153.11, 148.79, 146.47, 145.20, 142.95, 140.64, 135.35, 135.31, 124.55, 123.67, 120.89, 120.00, 118.92, 109.60, 100.65, 99.45, 78.09, 68.57, 52.82, 49.60, 41.83, 36.71, 36.30, 35.63, 35.15, 31.41, 31.34, 29.71, 28.90, 28.12, 27.74, 27.34, 25.72, 25.49, 23.83, 23.17, 22.62, 22.36, 20.58, 19.05, 18.53, 11.65. MS (ESI) calculated for $C_{68}H_{77}Na_7O_{36}S_7$, $[(M-2Na)]^{2-}$, m/z 904.08, found for $[(M+H)]^+$, 904.35.

We claim:

1. A compound of Formula I:

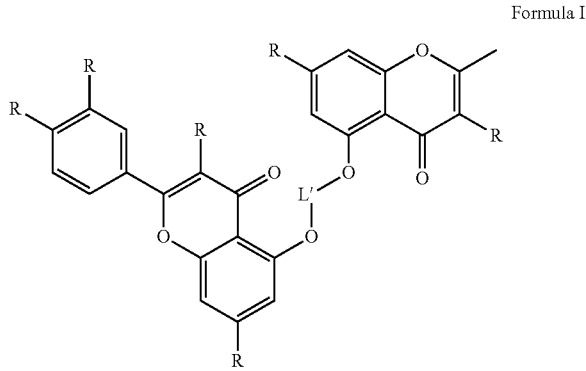

Formula I

-continued

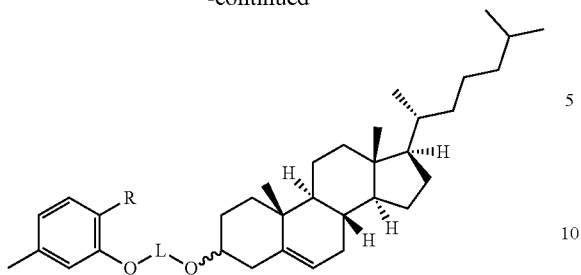

wherein:
R at each location is the same or different and is hydrogen, —OH, or —OSO$_3^-$M$^+$ with the caveat that at least one R is -OSO$_3^-$M$^+$, wherein M$^+$ is a cation selected from the group consisting of Na$^+$, K$^+$, Li$^+$, Ca$^{2+}$, and NG$_4^+$, wherein G is H, an alkyl group, an alicyclic group or an aryl group;

L and L' are the same or different and are selected from the group consisting of:

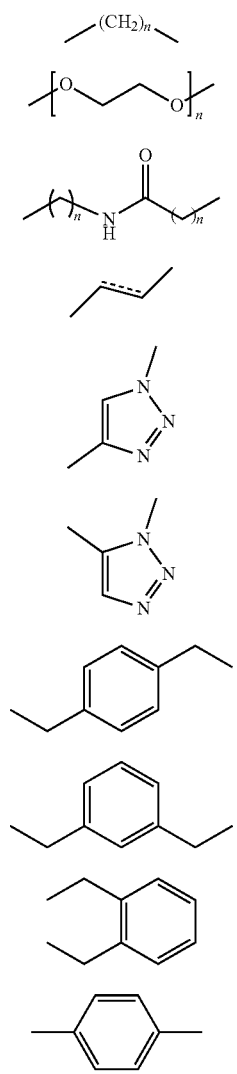

L1
L2
L3
L4
L5
L6
L7
L8
L9
L10

 L11

 L12

 L13

 L14

 L15

 L16

 L17

 L18

 L19 n is an integer from 1 to 18;
the non-straight line represents a bond of undefined stereochemistry;
or a pharmaceutically acceptable salt, solvate or hydrate thereof.

2. The compound of claim 1, having the structure of Formula II:
Formula II
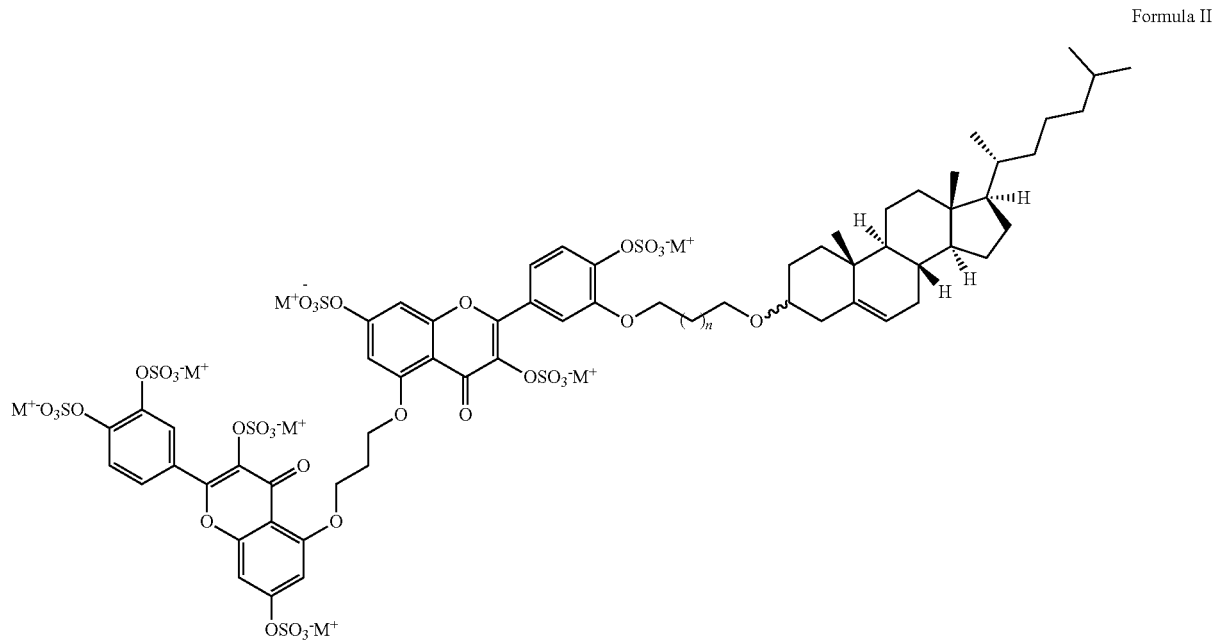
wherein,
n is an integer from 1 to 18; and
the non-straight line represents a bond of undefined stereochemistry.
3. The compound of claim 1 having the structure of Formula IIa:
Formula IIa
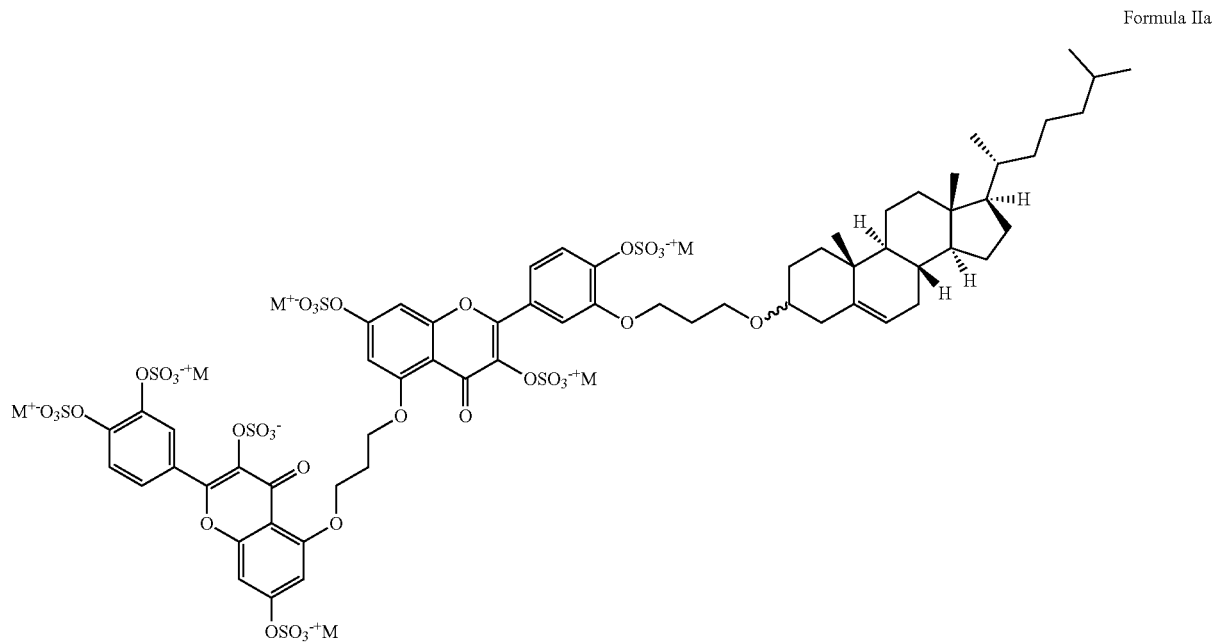
wherein the non-straight line represents a bond of undefined stereochemistry.

4. The compound of claim 1 having the structure of Formula IIb:

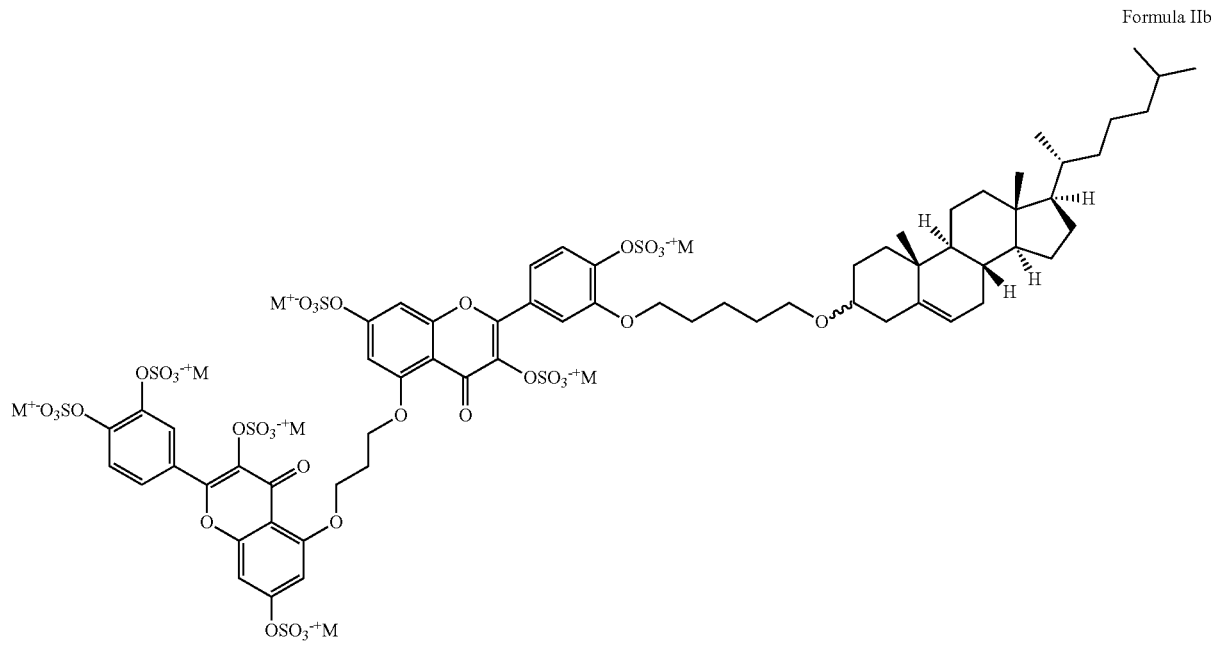

Formula IIb wherein the non-straight line represents a bond of undefined stereochemistry.

5. The compound of claim 1 having the structure of Formula IIc:

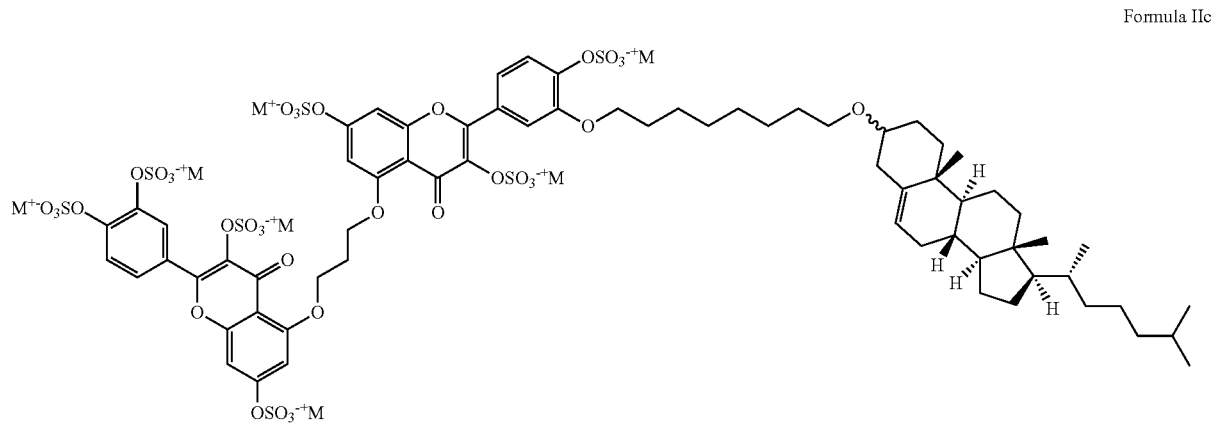

Formula IIc wherein the non-straight line represents a bond of undefined stereochemistry.

6. A method for treating colon and/or lung cancer comprising administering to a subject in need thereof a therapeutically effective amount of a compound of claim 1.

7. The method of claim 6, wherein the subject is mammalian.

8. The method of claim 6, wherein the subject is human.

9. A method of synthesizing a compound of Formula II:

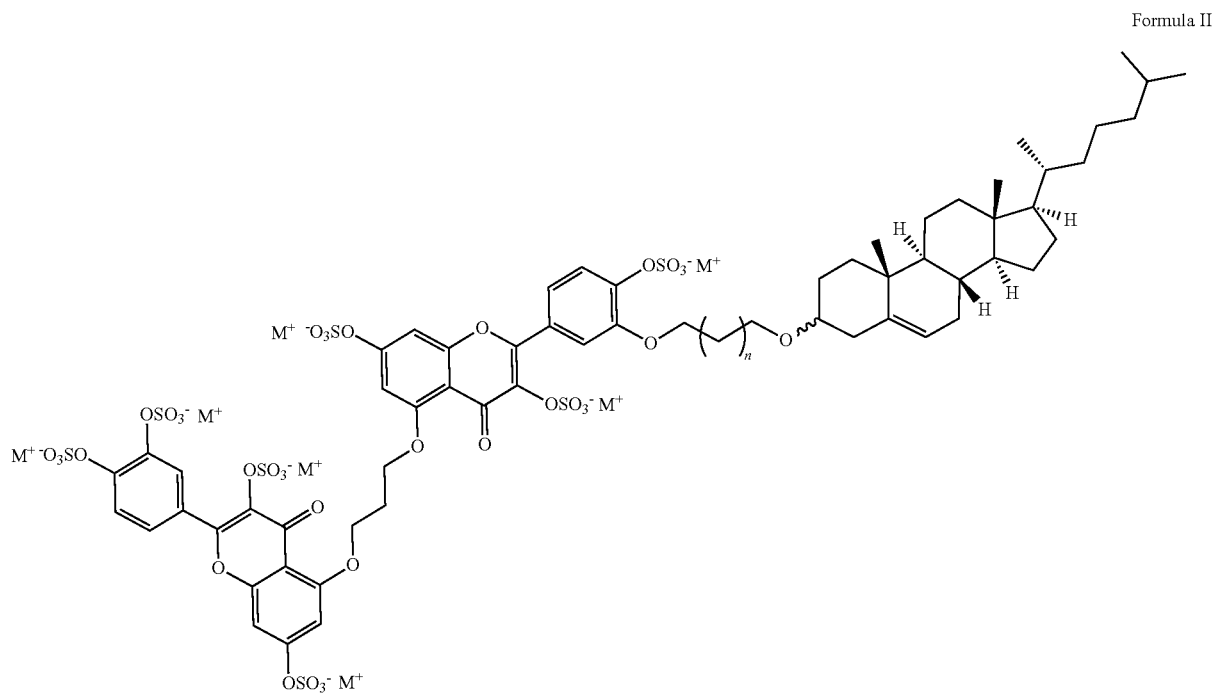

Formula II wherein n is an integer from 1 to 18, the non-straight line represents a bond of undefined stereochemistry and $M^+$ is a cation selected from the group consisting of $Na^+$, $K^+$, $Li^+$, $Ca^{2+}$, and $NG_4^+$, wherein G is H, an alkyl group, an alicyclic group or an aryl group;

comprising the steps of i) protecting cholesterol with protecting group Z, to form intermediate 1a:

ii) reacting intermediate 1a with a diol:

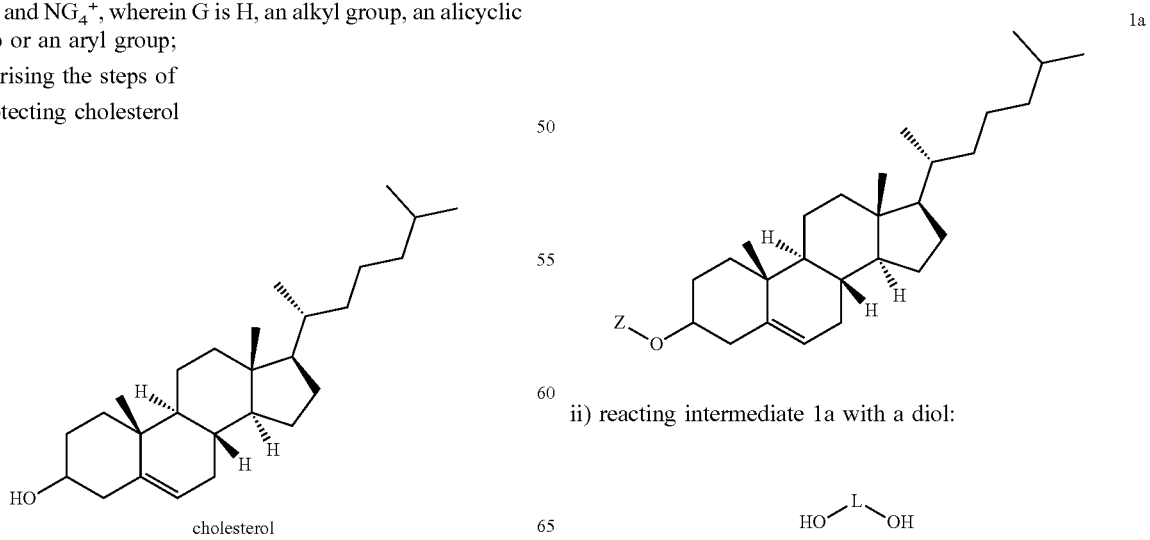

wherein L is a linker selected from the group consisting of:
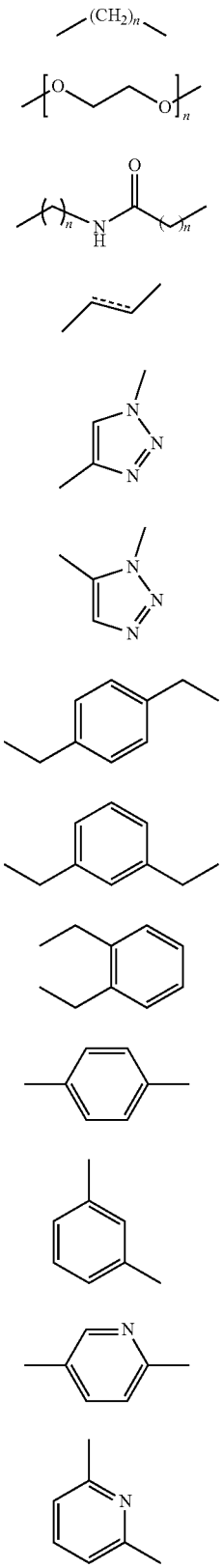
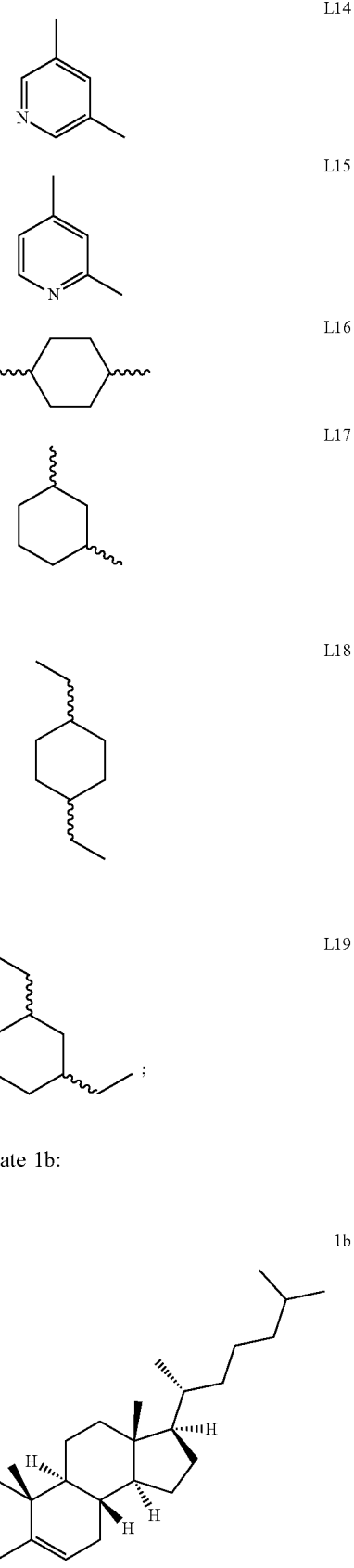
to form intermediate 1b:

iii) protecting intermediate 1b with protecting group Z' to form intermediate 1c:
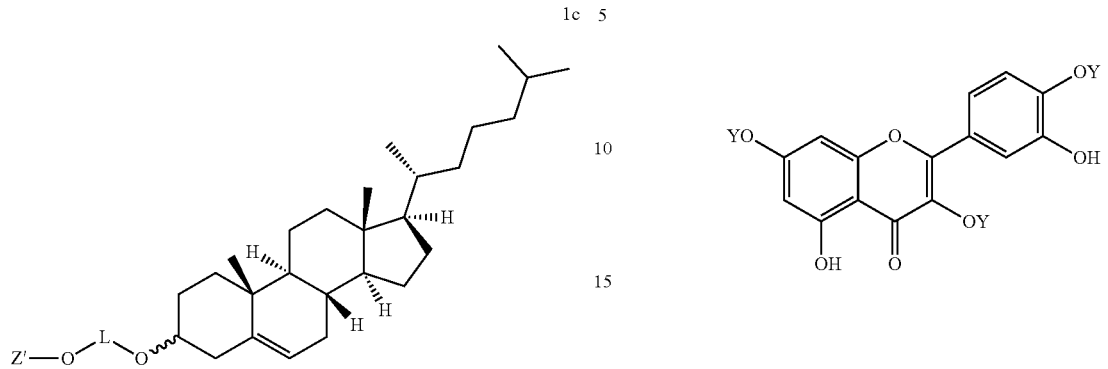
iv) reacting intermediate 1c with a triprotected quercetin of formula
to form intermediate 1d,
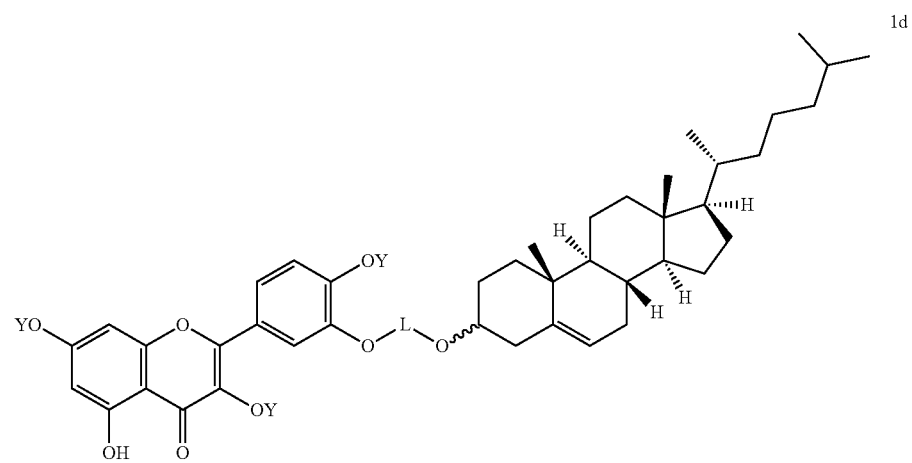
wherein Y is a protecting group;
v) reacting intermediate 1d with a compound of formula:
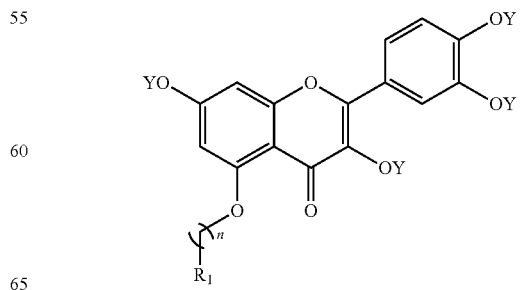

wherein R1 is a halogen or a tosylate and n is an integer from 1 to 18;

to form intermediate 1e

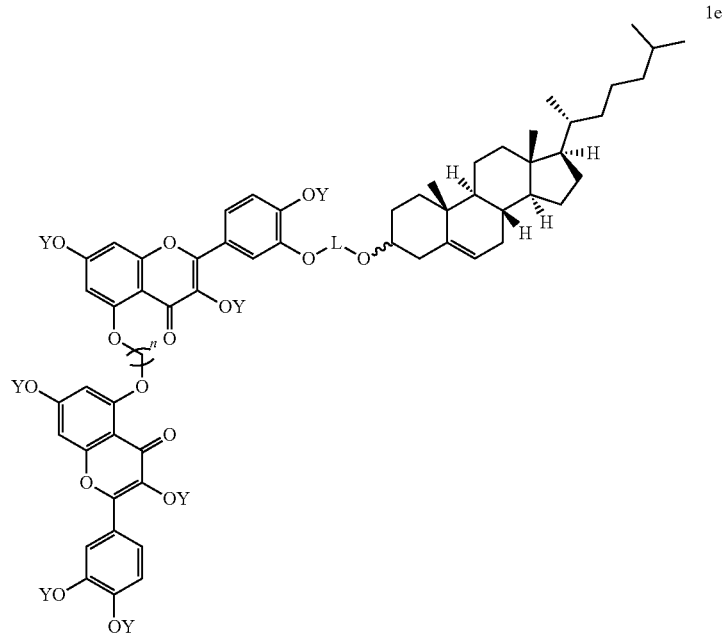

and vi) deprotecting and sulfating intermediate 1e to form the compound of Formula II;

wherein the protecting groups Z, Z' and Y are the same or different and are selected from the group consisting of 4-toluenesulfonyl, methyl, methoxymethyl, benzoyl, benzyl, silyl, p-methoxybenzyl, tetrahydropyranyl, t-butyl, allyl, t-butyldimethylsilyl, t-butylphenylsilyl, acetyl and pivaloyl.

10. The method of claim 9, wherein at least one of steps i) to vi) is conducted under microwave conditions in a batch reactor mode or a flow reactor mode.

11. The method of claim 9, wherein the halogen is Br, Cl or I.

* * * * *